(12) United States Patent
Rabiner et al.

(10) Patent No.: US 9,216,049 B2
(45) Date of Patent: Dec. 22, 2015

(54) SYSTEMS AND METHODS FOR IMPLANT REMOVAL

(75) Inventors: Robert A. Rabiner, Tiverton, RI (US); Gene P. DiPoto, Upton, MA (US); Jeffrey P. Broussaeau, Barrington, RI (US); Augustus C. Shanahan, Newton, MA (US); Chi Yin Wong, Canton, MA (US); Anthony T. O'Leary, Walpole, MA (US)

(73) Assignee: IlluminOss Medical, Inc., East Providence, RI (US)

( * ) Notice: Subject to any disclaimer, the term of this patent is extended or adjusted under 35 U.S.C. 154(b) by 410 days.

(21) Appl. No.: 13/297,097

(22) Filed: Nov. 15, 2011

(65) Prior Publication Data

US 2012/0150190 A1 Jun. 14, 2012

Related U.S. Application Data

(60) Provisional application No. 61/413,711, filed on Nov. 15, 2010.

(51) Int. Cl.
*A61B 17/92* (2006.01)
*A61B 17/16* (2006.01)
(Continued)

(52) U.S. Cl.
CPC .............. *A61B 17/921* (2013.01); *A61B 17/164* (2013.01); *A61B 17/1615* (2013.01); *A61B 17/7275* (2013.01); *A61B 17/8872* (2013.01); *A61B 17/8897* (2013.01); *A61B 17/1697* (2013.01); *A61B 17/1717* (2013.01); *A61B 17/864* (2013.01); *A61B 17/8875* (2013.01); *A61B 19/5244* (2013.01); *A61B 2017/005* (2013.01); *A61B 2017/00407* (2013.01); *A61B 2017/00464* (2013.01); *A61B 2017/00469* (2013.01); *A61B 2017/00836* (2013.01); *A61B 2017/00867* (2013.01); *A61B 2017/1602* (2013.01); *A61B 2019/307* (2013.01)

(58) Field of Classification Search
CPC ............... A61B 17/88; A61B 17/8811; A61B 17/8841; A61B 17/8861; A61B 17/8897; A61B 17/92; A61B 17/921; A61B 17/164; A61B 17/1657; A61B 17/1662; A61B 17/1668; A61B 17/1675; A61B 17/1677; A61B 17/16
See application file for complete search history.

(56) References Cited

U.S. PATENT DOCUMENTS 4,294,251 A 10/1981 Greenwald et al.
4,919,153 A * 4/1990 Chin ............................... 606/93
(Continued)

OTHER PUBLICATIONS

PCT International Search Report based on PCT/US2011/060870 dated Feb. 23, 2012.

*Primary Examiner* — Samuel Hanna
(74) *Attorney, Agent, or Firm* — Greenberg Traurig, LLP; David J. Dykeman; Roman Fayerberg

(57) ABSTRACT

Implant removal systems and methods for using the system for removing an implant from a bone are disclosed herein. In an embodiment, a method for removing an intramedullary implant from a bone includes navigating a guidewire into an intramedullary cavity of the bone; inserting the guidewire into a lumen of an intramedullary implant located in the intramedullary cavity of the bone; advancing a removal screw over the guidewire to the intramedullary implant; threading the removal screw into the lumen of the intramedullary implant to engage the removal screw to the intramedullary implant; and applying impaction force on the removal screw to remove the intramedullary implant from the intramedullary cavity.

9 Claims, 41 Drawing Sheets

(51) Int. Cl.
*A61B 17/72* (2006.01)
*A61B 17/88* (2006.01)
*A61B 17/17* (2006.01)
*A61B 17/86* (2006.01)
*A61B 19/00* (2006.01)
*A61B 17/00* (2006.01)

(56) References Cited

U.S. PATENT DOCUMENTS

| | | | |
|---|---|---|---|
| 5,222,957 A * | 6/1993 | McColl et al. | 606/86 R |
| 5,222,958 A * | 6/1993 | Chin | A61B 17/1628 606/100 |
| 5,520,668 A | 5/1996 | Greff et al. | |
| 5,554,111 A | 9/1996 | Morrey et al. | |
| 5,707,374 A | 1/1998 | Schmidt | |
| 6,336,930 B1 * | 1/2002 | Stalcup et al. | 606/284 |
| 6,358,252 B1 | 3/2002 | Shapira | |
| 6,425,923 B1 * | 7/2002 | Stalcup et al. | 623/23.58 |
| 6,478,751 B1 | 11/2002 | Krueger et al. | |
| 6,908,455 B2 | 6/2005 | Hajianpour | |
| 7,481,791 B2 | 1/2009 | Cover et al. | |
| 7,632,277 B2 | 12/2009 | Woll et al. | |
| 2008/0287951 A1 | 11/2008 | Stoneburner et al. | |
| 2009/0228007 A1 | 9/2009 | Justin et al. | |
| 2010/0262069 A1 | 10/2010 | Rabiner et al. | |

* cited by examiner

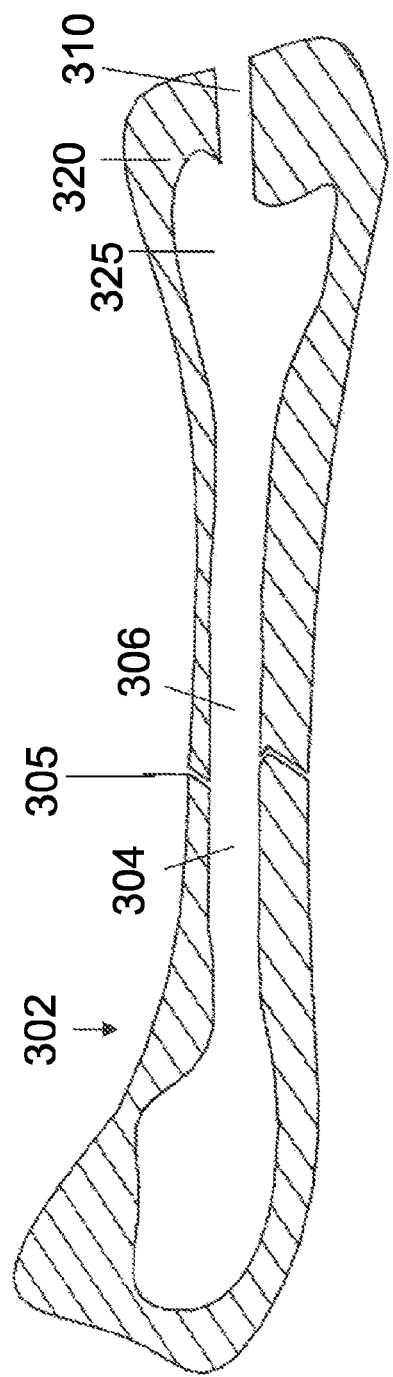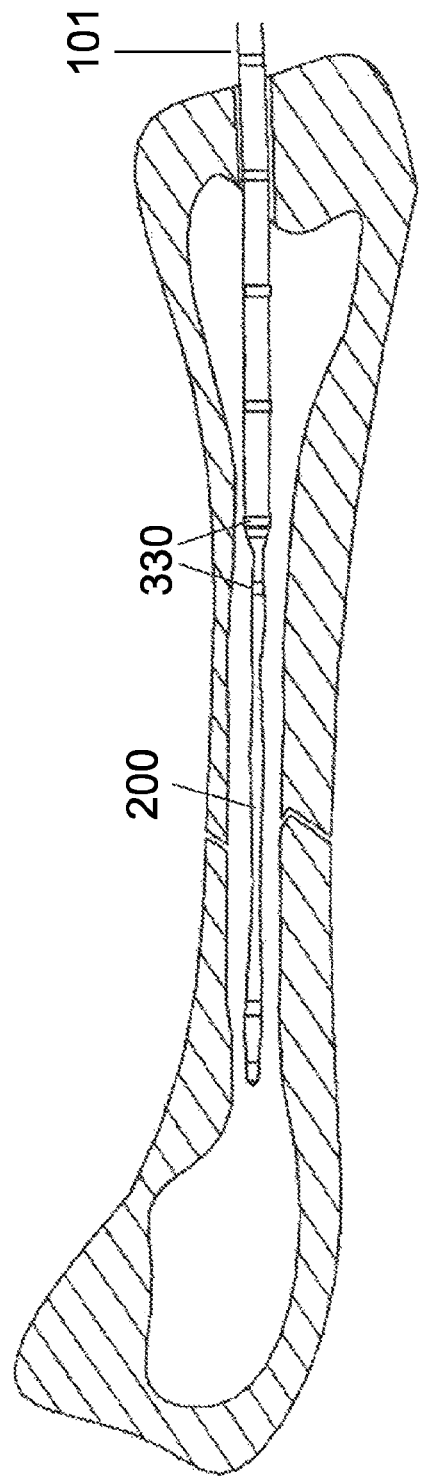
FIG. 3A
FIG. 3B

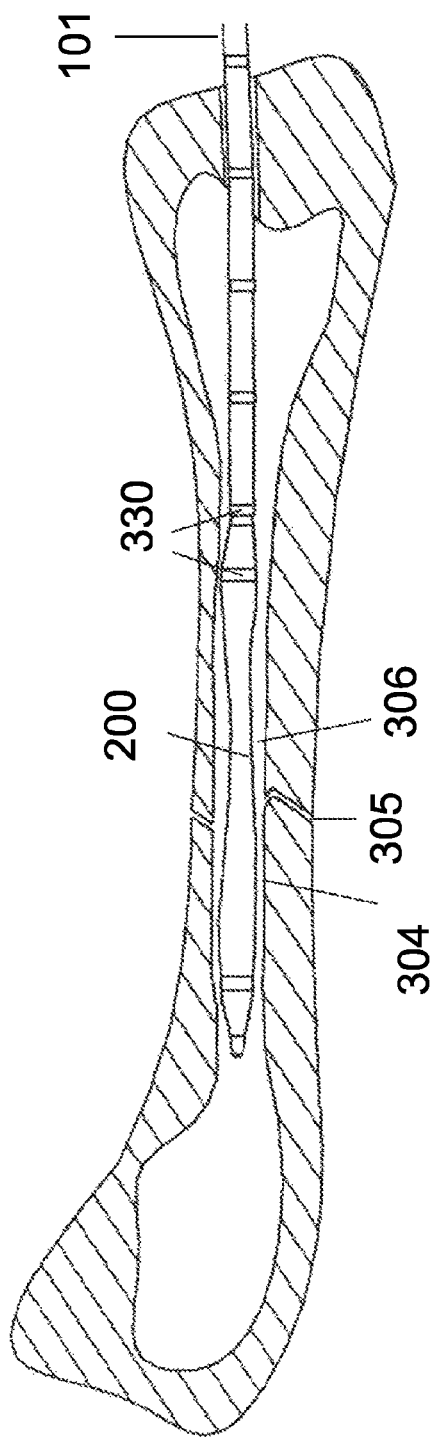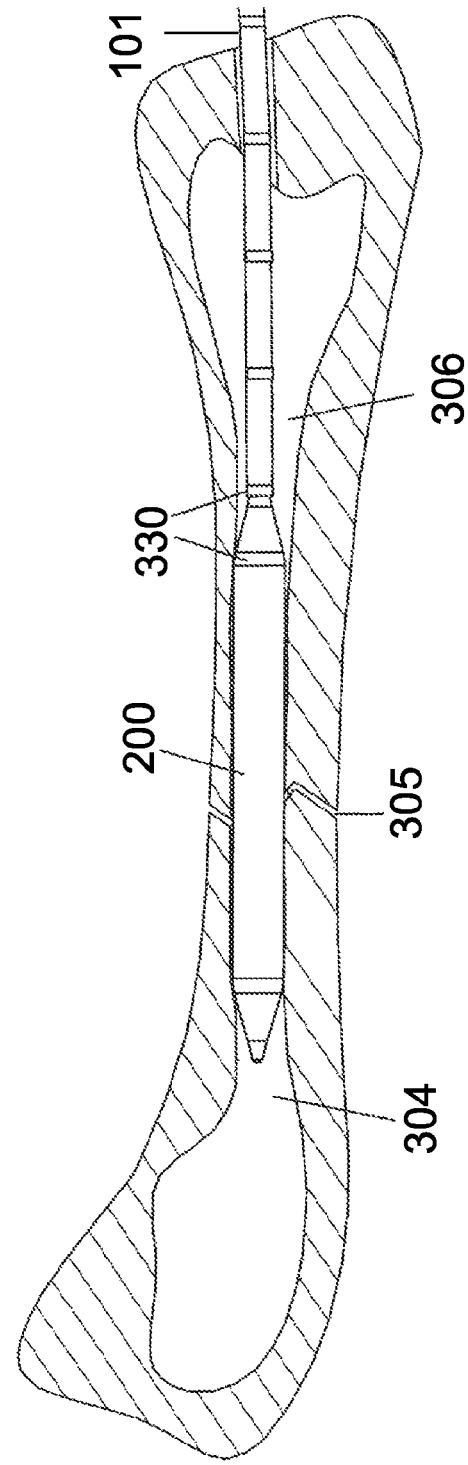

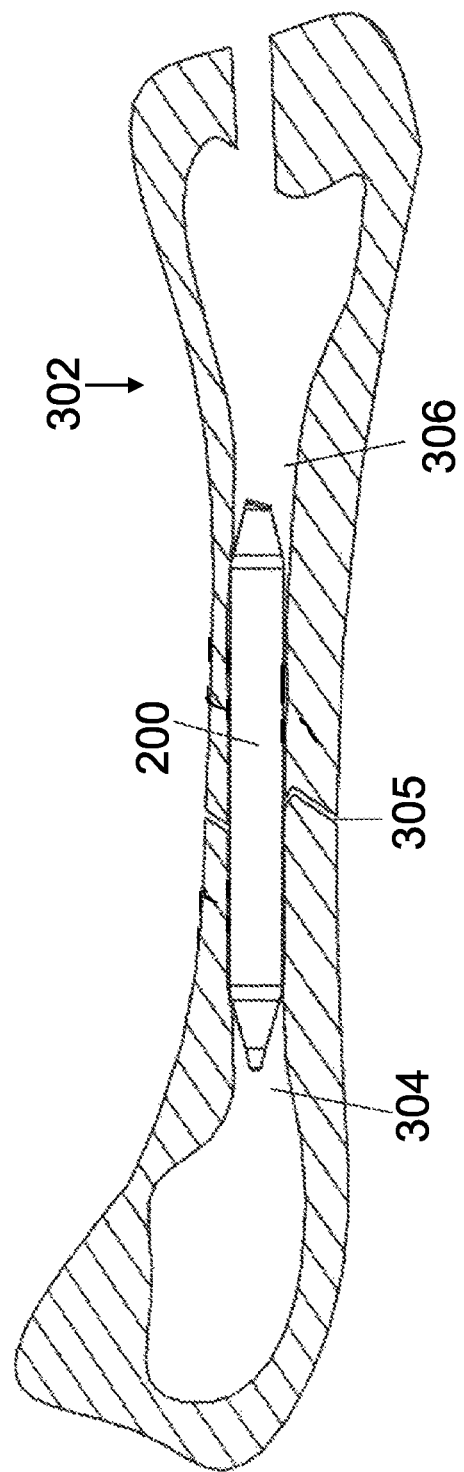

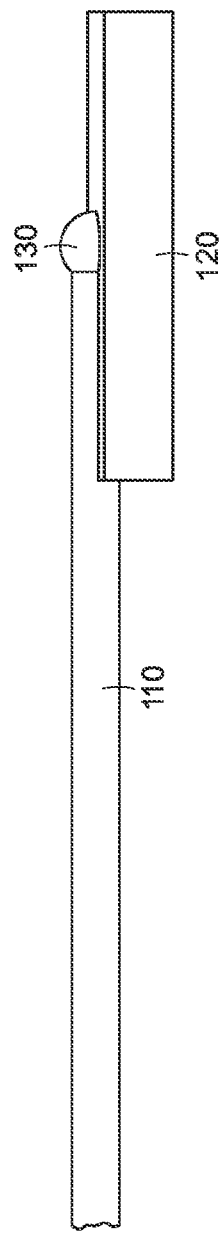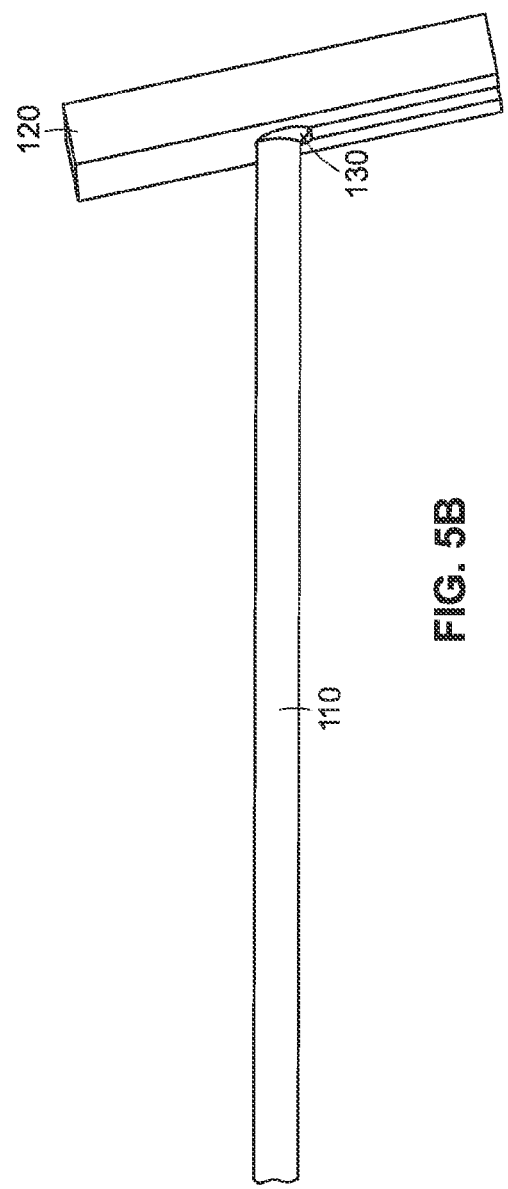

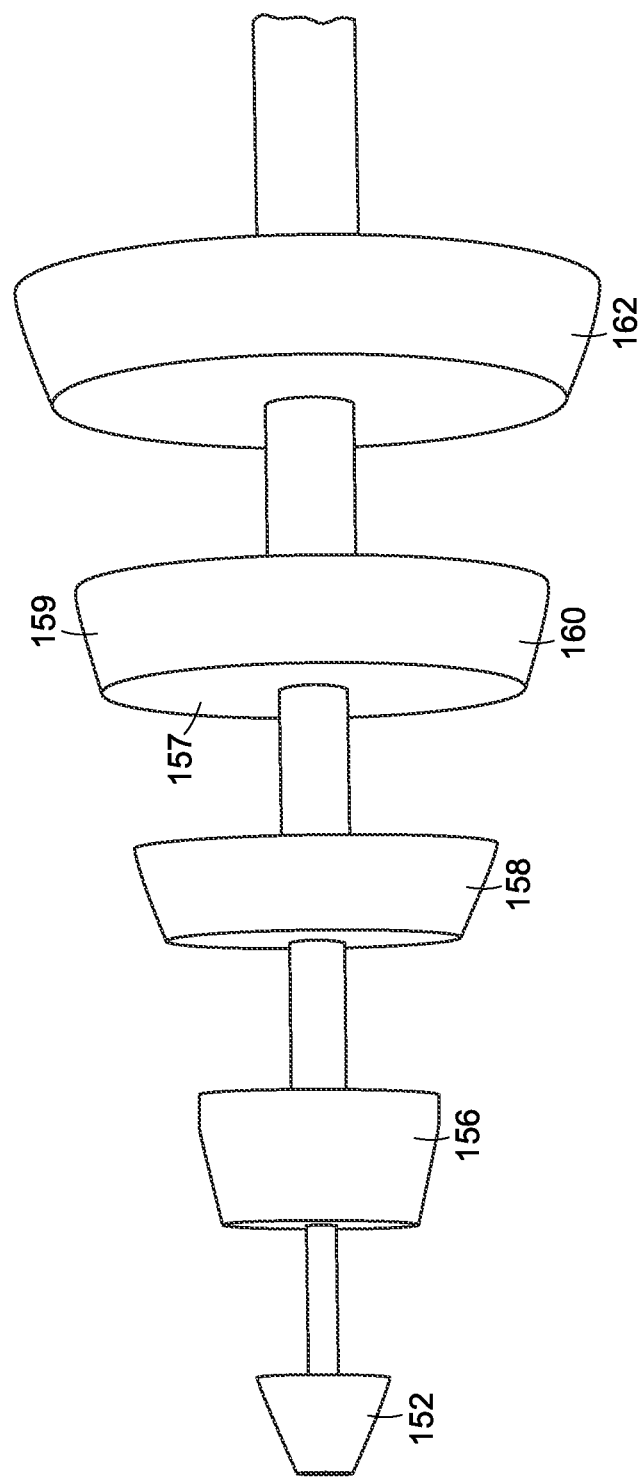

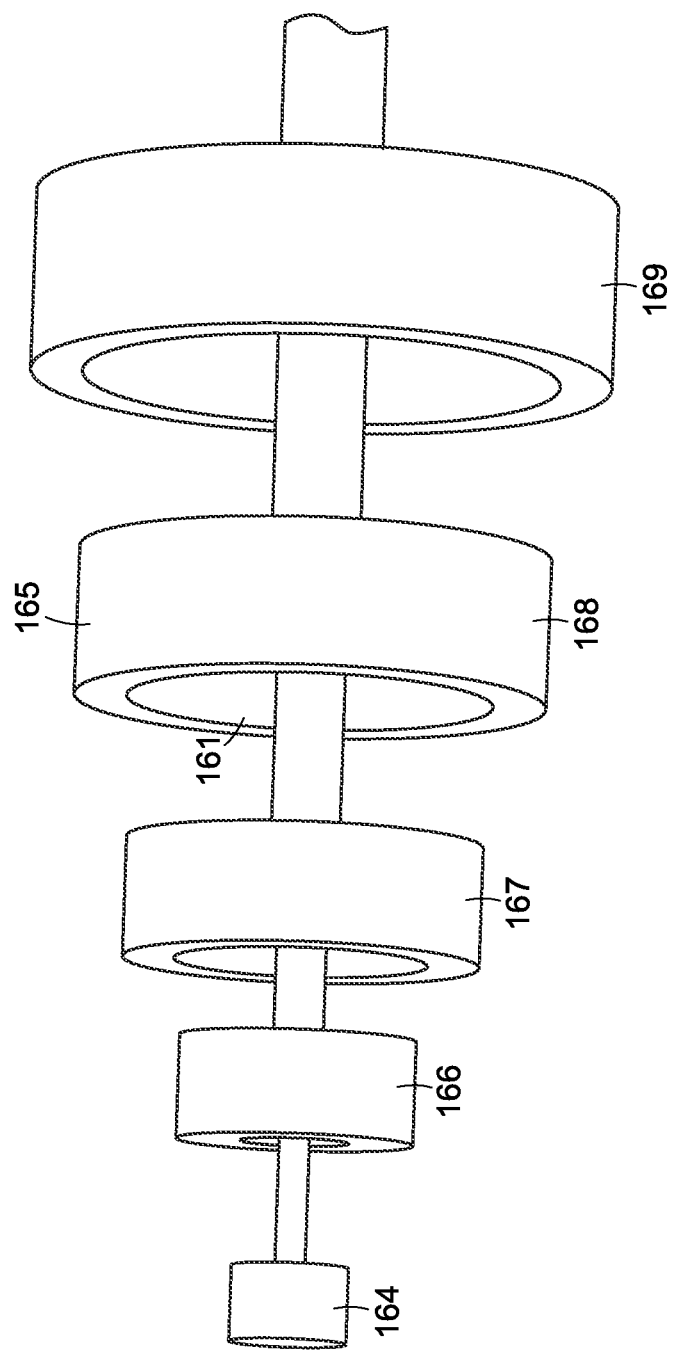

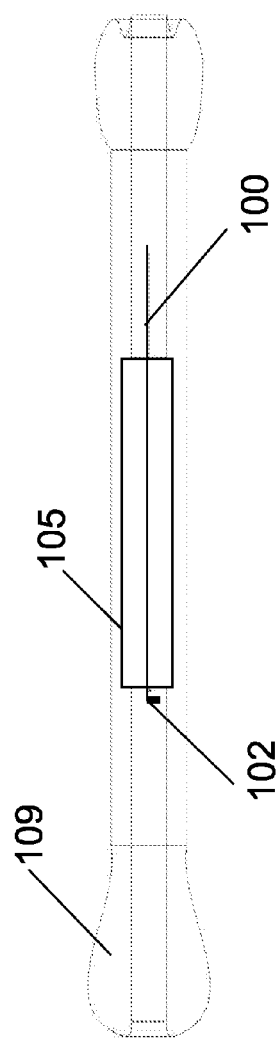
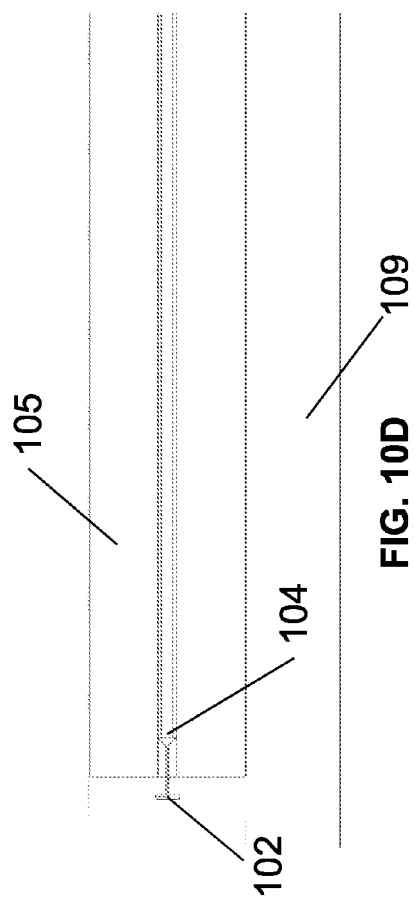
FIG. 10C
FIG. 10D

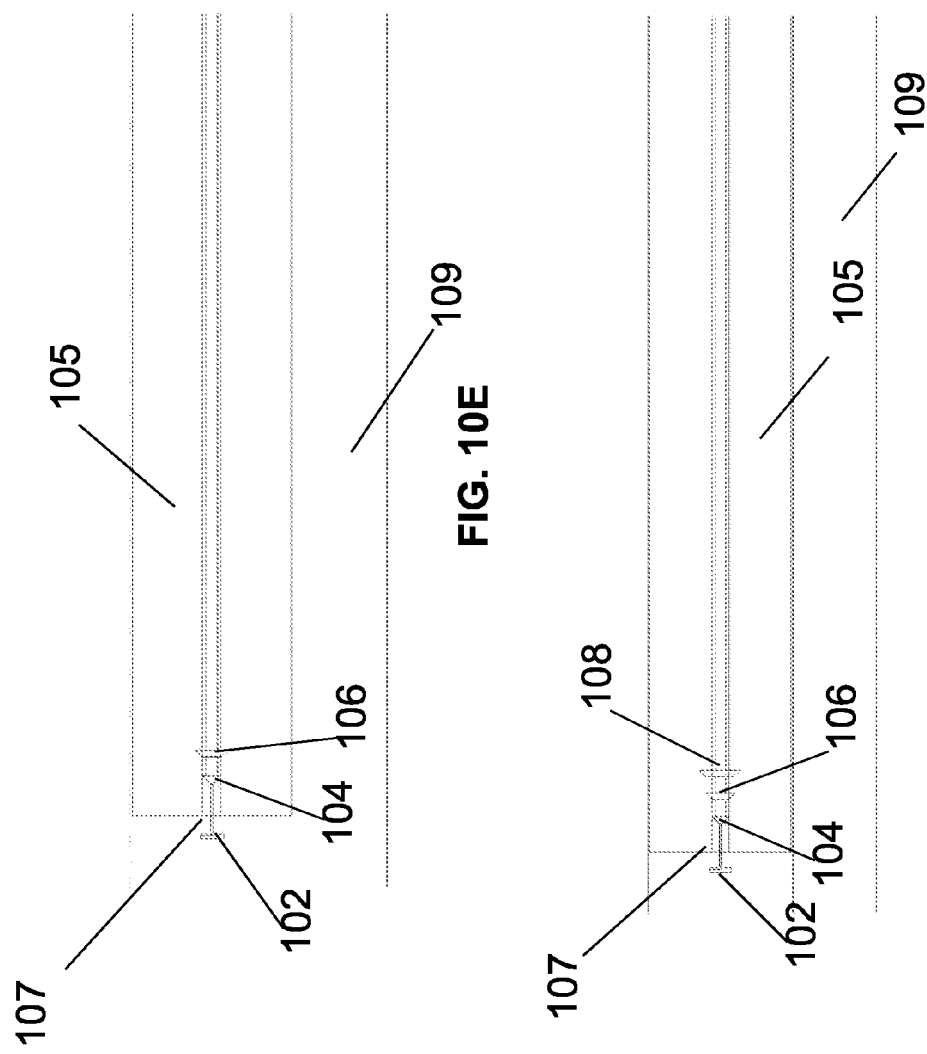

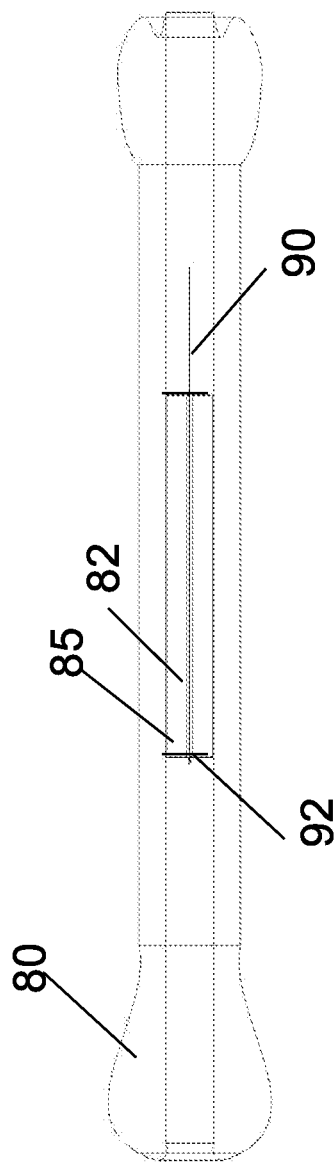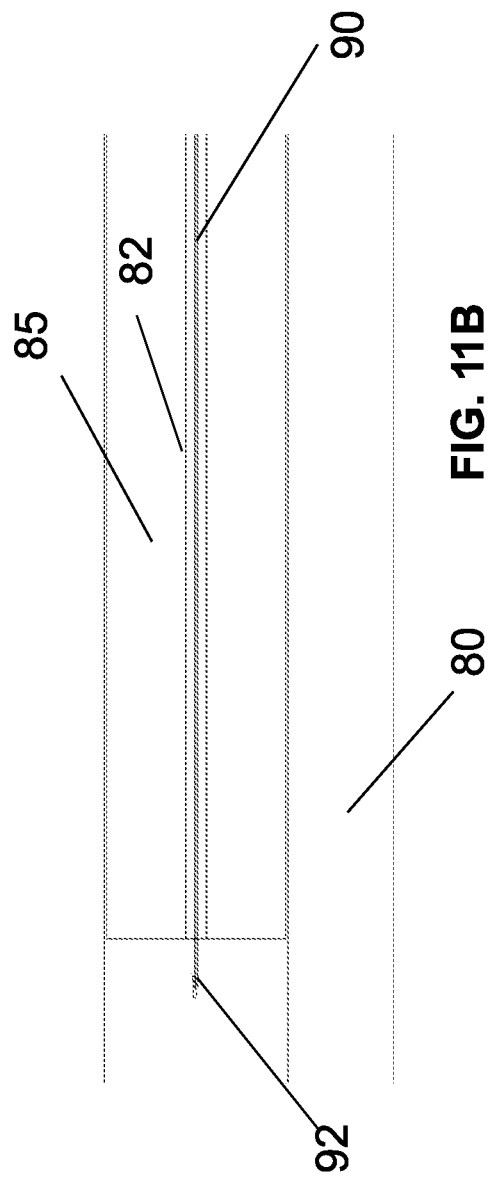

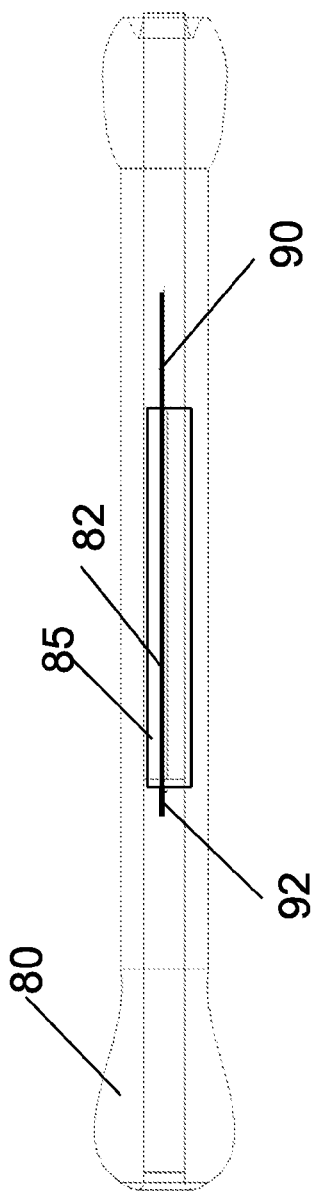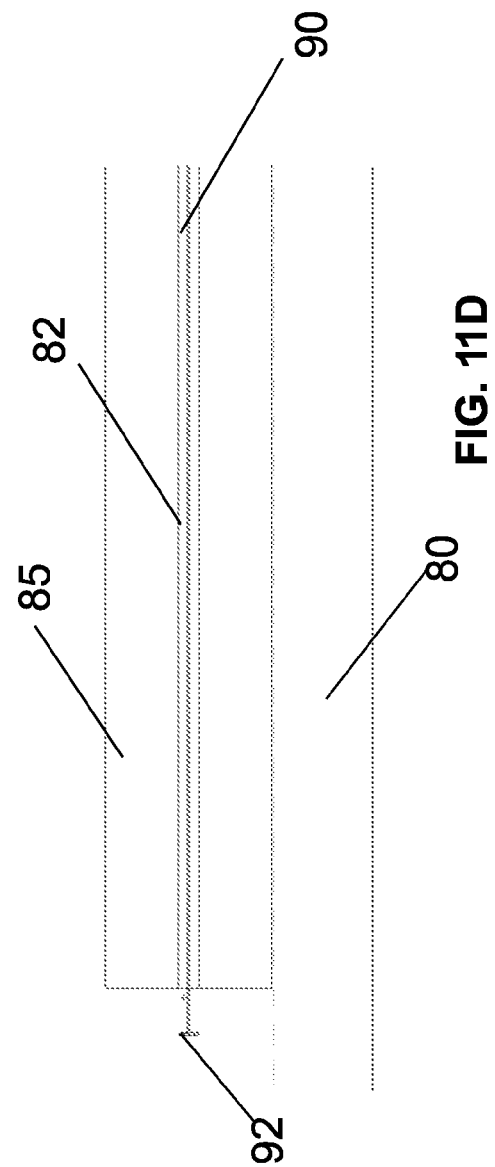

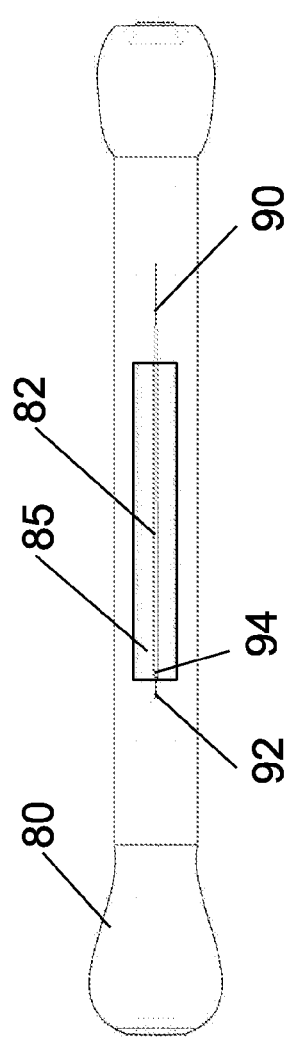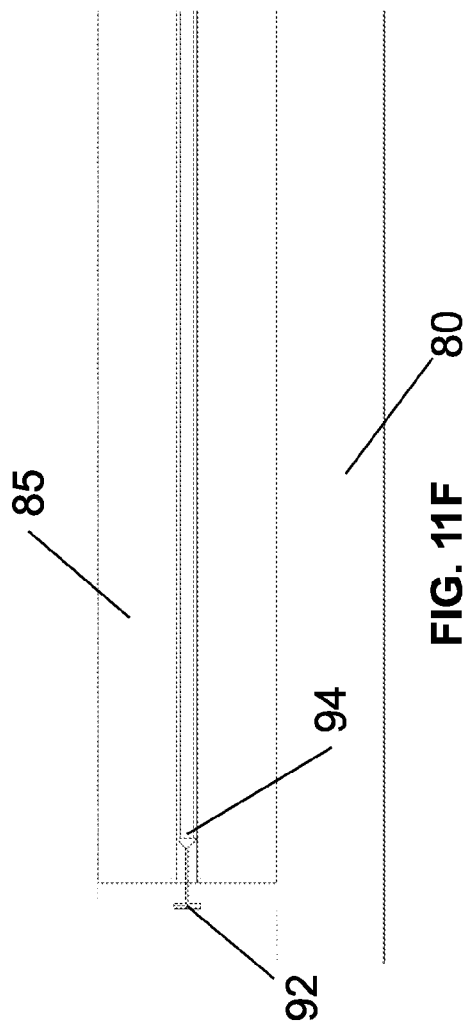
FIG. 11E
FIG. 11F

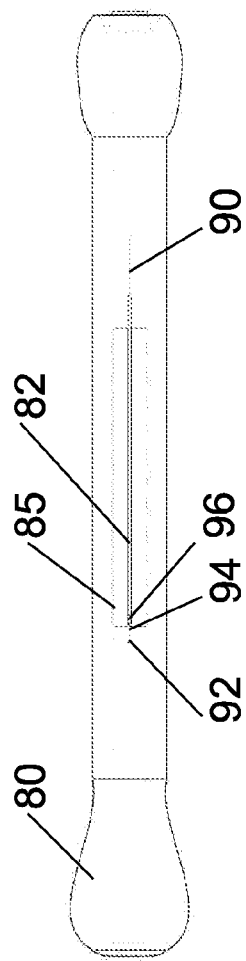
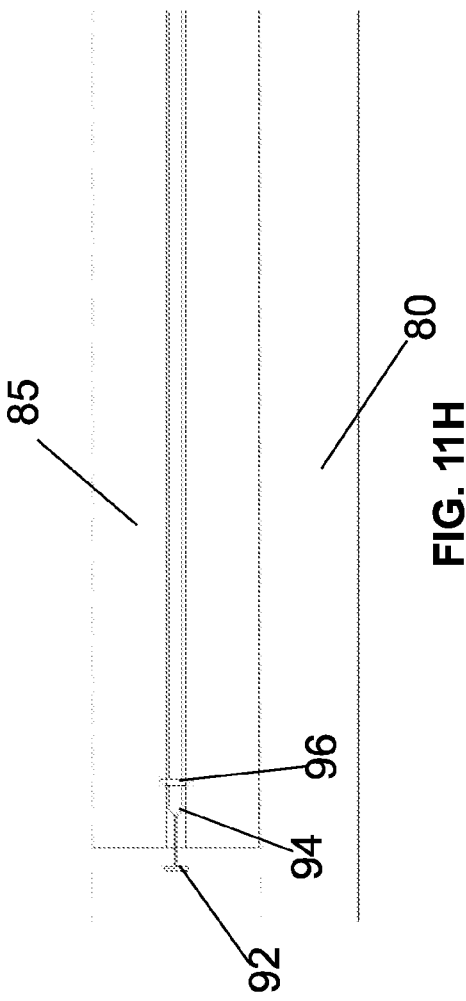
FIG. 11G
FIG. 11H

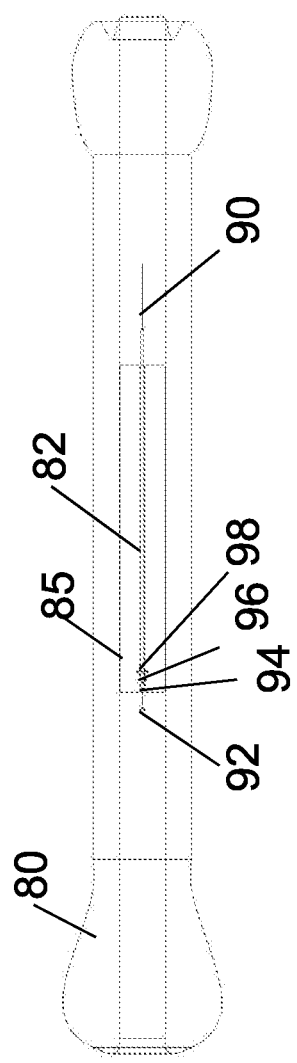
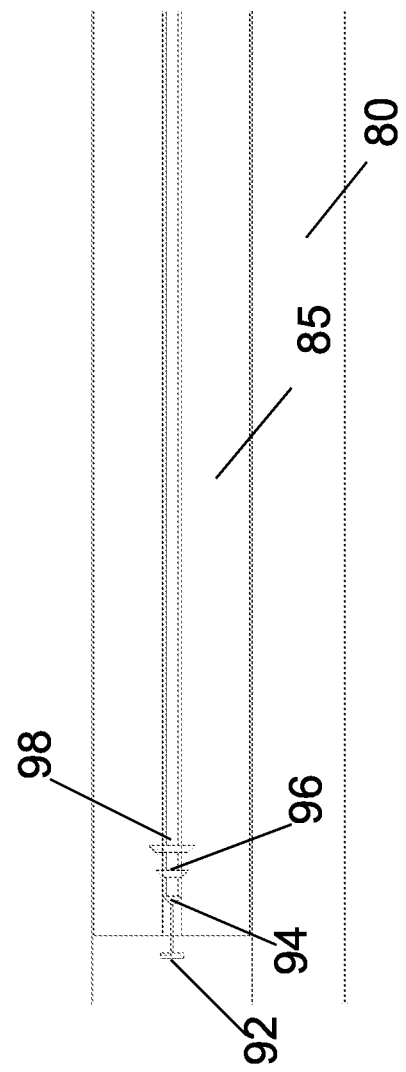
FIG. 11I
FIG. 11J

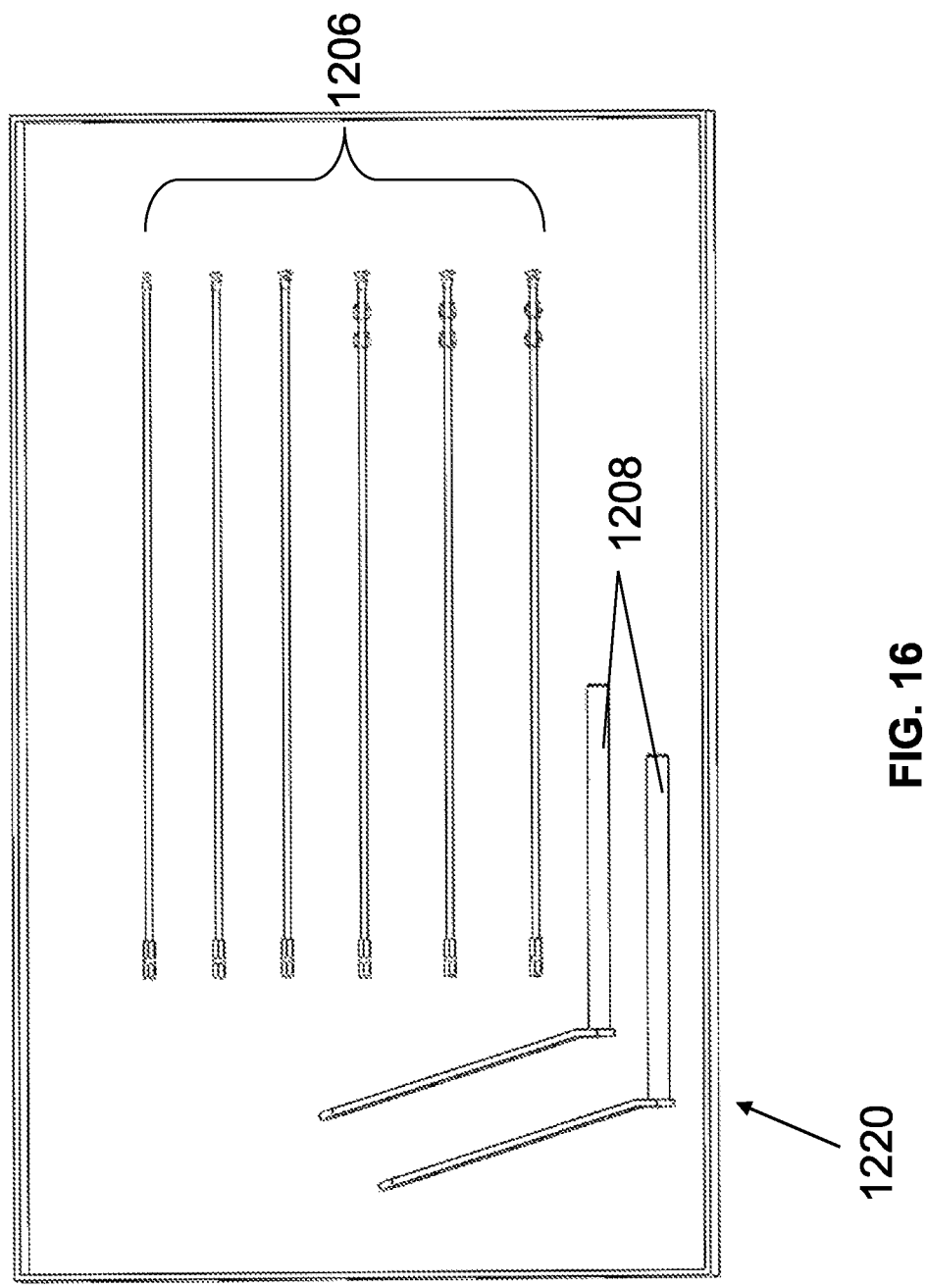

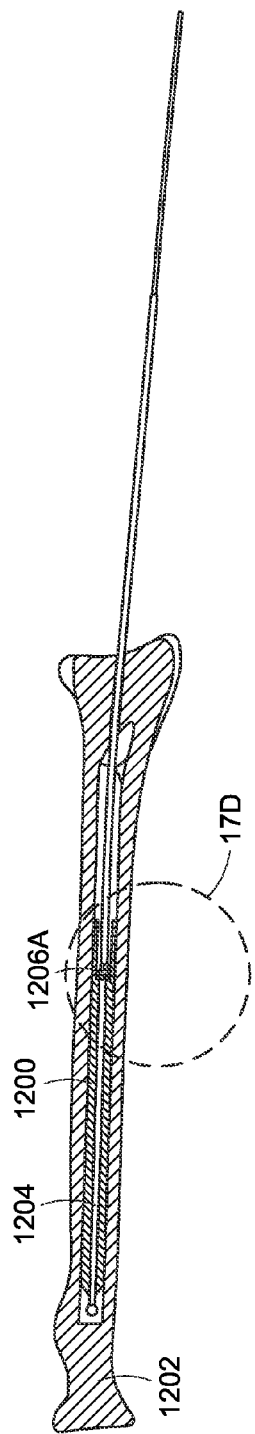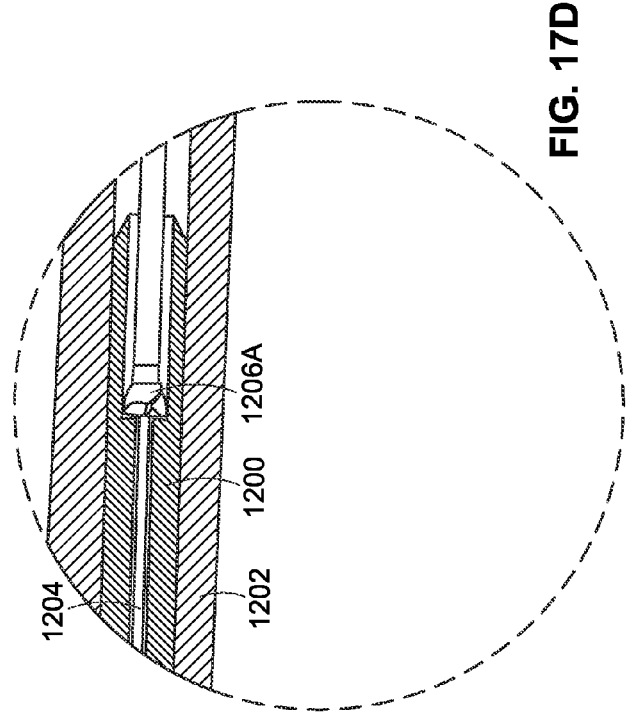
FIG. 17C
FIG. 17D

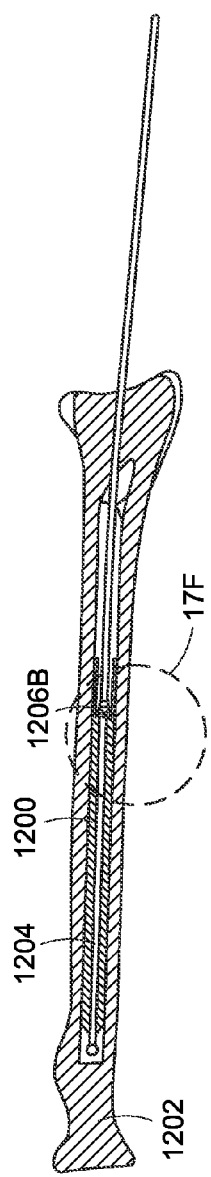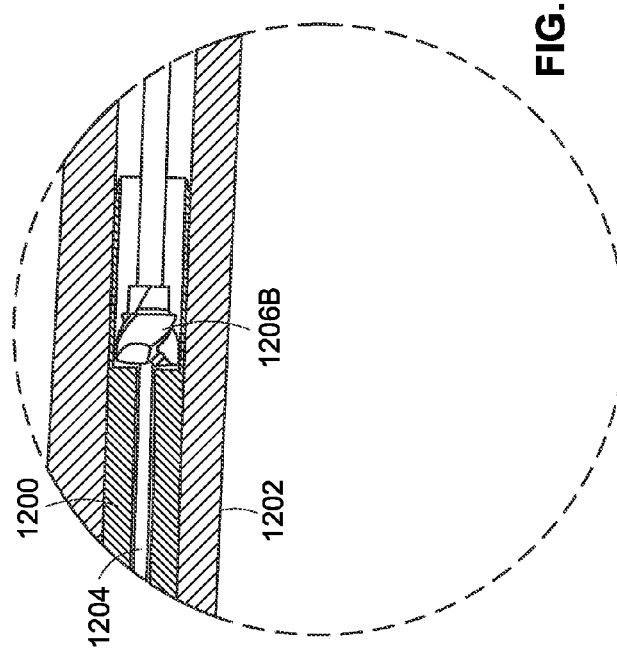
FIG. 17E
FIG. 17F

SYSTEMS AND METHODS FOR IMPLANT REMOVAL

RELATED APPLICATIONS

This application claims the benefit of and priority from U.S. Provisional Application No. 61/413,711, filed on Nov. 15, 2010, the entirety of which is incorporated herein by reference for the teachings therein.

FIELD

The embodiments disclosed herein relate to implant removal systems, and more particularly to intramedullary implant removal systems and osteotomy implant removal systems and methods for using the system for removing an implant from within a bone.

BACKGROUND

Bones form the skeleton of the body and allow the body to be supported against gravity and to move and function in the world. Bone fractures can occur, for example, from an outside force or from a controlled surgical cut (an osteotomy). A fracture's alignment is described as to whether the fracture fragments are displaced or in their normal anatomic position. In some instances, surgery may be required to re-align, stabilize and distract the fractured bone.

Fracture repair is the process of rejoining and realigning the ends of broken bones. Fracture repair is required when there is a need for restoration of the normal position and function of the broken bone. Throughout the stages of fracture healing, the bones must be held firmly in the correct position and supported until the bone is strong enough to bear weight. In the event the fracture is not properly repaired, malalignment of the bone may occur, resulting in possible physical dysfunction of the bone or joint of that region of the body. Various implants can be used to in the process of rejoining and realigning broken bones. Once the bone has heeled or the implant requires replacing, it may be desired to remove the implant from the bone.

SUMMARY

Implant removal systems and methods for using the system for removing an implant from a bone are disclosed herein. According to aspects illustrated herein, there is provided a method for removing an intramedullary implant from a bone comprising: navigating a guidewire into an intramedullary cavity of the bone; inserting the guidewire into a lumen of an intramedullary implant located in the intramedullary cavity of the bone; advancing a removal screw over the guidewire to the intramedullary implant; threading the removal screw into the lumen of the intramedullary implant to engage the removal screw to the intramedullary implant; and applying impaction force on the removal screw to remove the intramedullary implant from the intramedullary cavity.

According to aspects illustrated herein, there is provided a method for removing an intramedullary implant from a bone that includes advancing a guidewire into an intramedullary cavity of a bone; inserting the guidewire into a lumen of an intramedullary implant located in the intramedullary cavity of the bone; advancing a first auger having a first diameter over the guidewire toward the intramedullary implant; and engaging the first auger to a distal end of the intramedullary implant to remove at least a portion of the intramedullary implant.

According to aspects illustrated herein, there is provided a system for removal of an implant from a bone comprising: one or more guidewires sufficiently designed to be inserted into a lumen of an intramedullary implant in a bone; one or more removal screws, wherein the removal screws are cannulated such that the removal screws can be advanced over the guidewire to the intramedullary implant; the removal screws include a threaded distal portion for engagement of the implant; and a slaphammer designed to engage the removal screws and to apply an impaction force on the removal screw engaged to the intramedullary implant to remove the intramedullary implant from the bone.

BRIEF DESCRIPTION OF THE DRAWINGS

The presently disclosed embodiments will be further explained with reference to the attached drawings, wherein like structures are referred to by like numerals throughout the several views. The drawings shown are not necessarily to scale, with emphasis instead generally being placed upon illustrating the principles of the presently disclosed embodiments.

FIGS. 3A-3E show an embodiment of method steps for implanting an expandable portion of an intramedullary device that can be removed according to the methods of the present disclosure.

FIG. 5A and FIG. 5B show perspective views of a toggle component of the system of FIG. 1.

FIG. 8 shows a side view of an embodiment of the burr components of an implant removal system of the present disclosure.

FIG. 9A, FIG. 9B and FIG. 9C show a side view of an embodiment of the burr components of an implant removal system of the present disclosure.

FIGS. 10A-10F show an embodiment of method steps for removal of an implant using an implant removal system of the present disclosure.

FIGS. 11A-11J show an embodiment of method steps for removal of an implant using an implant removal system of the present disclosure.

FIG. 16 shows an embodiment of a kit of the present disclosure for removal of an intramedullary device from a bone.

FIGS. 17A-17F show an embodiment of method steps for removing an intramedullary device from a bone using the embodiment kit of FIG. 16.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

Systems and methods for removing an intramedullary implant are disclosed herein. In an embodiment, the implant comprises an expandable portion comprising a hardened reinforcing mixture, such as a hardened light sensitive liquid. In an embodiment, the expandable portion has a central lumen therethrough.

Figure 1:
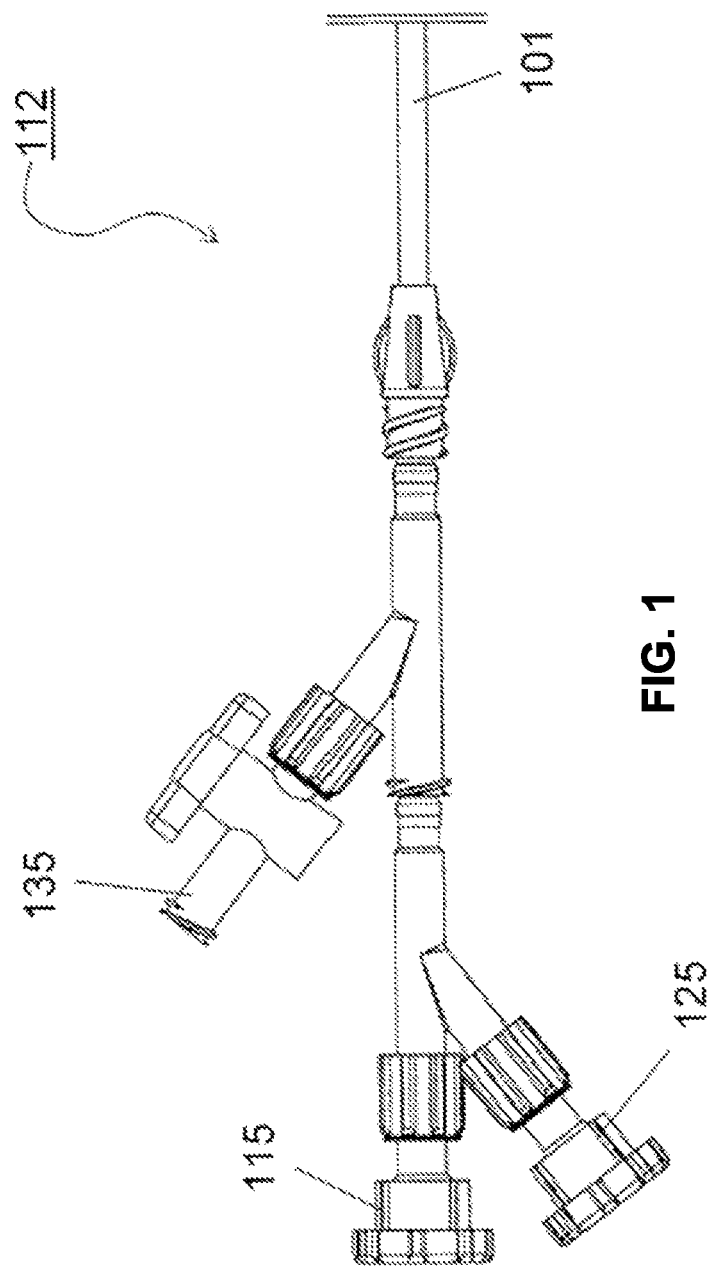
FIG. 1 is a side view of an embodiment of a proximal end of an apparatus for insertion of an expandable portion component of an intramedullary implant that can be removed according to the methods of the present disclosure.

In an embodiment, a flexible insertion catheter may be used for insertion of an expandable portion component of an intramedullary implant that can be removed with removal systems of the present disclosure. Generally, such insertion catheters may include an elongated shaft with a proximal end and a distal end, and a longitudinal axis therebetween. FIG. 1 is a side view of an embodiment of a proximal end 112 of a flexible insertion catheter 101 of an apparatus of the present disclosure for insertion of an expandable portion of an intramedullary implant of the present disclosure. In an embodiment, the flexible insertion catheter 101 has an outer diameter from about 2 mm to about 8 mm. In an embodiment, the flexible insertion catheter 101 has an outer diameter from about 3 mm to about 6 mm.

Figure 2:
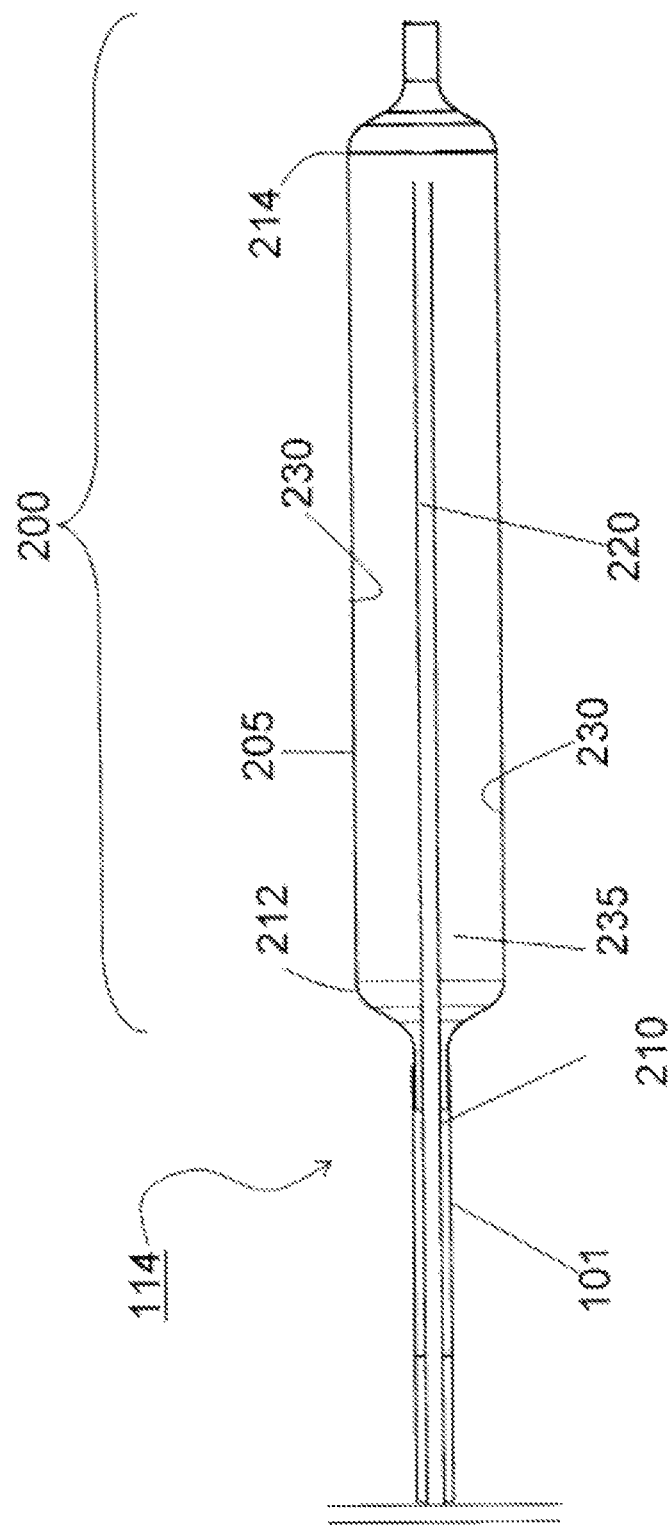
FIG. 2 is a side view of an embodiment of a distal end of an apparatus for insertion of an expandable portion component of an intramedullary implant that can be removed according to the methods of the present disclosure.

FIG. 2 is a side view of an embodiment of a distal end 114 of the flexible insertion catheter 101. The distal end 114 includes an expandable portion 200 releasably mounted on the flexible insertion catheter 101. The expandable portion 200 has an outer surface 205, an inner surface 230, and an inner cavity 235 defined by the inner surface 230. In an embodiment, the expandable portion 200 is manufactured from a thin-walled, non-compliant (non-stretch/non-expansion) conformable material. The expandable portion 200 may be formed of a pliable, resilient, conformable, and strong material, including but not limited to urethane, polyethylene terephthalate (PET), nylon elastomer and other similar polymers. In an embodiment, the expandable portion 200 of the present disclosure is constructed out of a PET nylon aramet or other non-consumable materials. The expandable portion 200 may be impregnated with a radiopaque material to enhance the visibility of the expandable portion 200. The expandable portion 200 is biocompatible, thus preventing or reducing possible adverse reactions after insertion into a fractured bone. In an embodiment, the expandable portion 200 is made from a material that is non-toxic, non-antigenic and non-immunogenic. The expandable portion 200 includes a proximal area 212 and a distal area 214. The proximal area 212 of the expandable portion 200 is releasably connected to the distal end 114 of the insertion catheter 101.

In an embodiment, a separation area is located at the junction between the expandable portion and the insertion catheter. The separation area may have a stress concentrator. The stress concentrator may be a notch, groove, channel or similar structure that concentrates stress in the separation area. The stress concentrator of the separation area may be notched, scored, indented, pre-weakened or pre-stressed to direct separation of the expandable portion from the elongated shaft of the insertion catheter under specific torsional load. The separation area ensures that there are no leaks of the light-sensitive liquid from the insertion catheter and/or the expandable portion. The separation area seals the expandable portion and removes the insertion catheter by making a break at a known or predetermined site (e.g., a separation area). The separation area may be various lengths and up to about an inch long. In an embodiment, when torque (twisting) is applied to the insertion catheter the shaft of the insertion catheter separates from the expandable portion. The twisting creates a sufficient shear to break the residual hardened light-sensitive and create a clean separation of the expandable portion/insertion catheter interface. In an embodiment, the expandable portion is cut from the insertion catheter using a cutting device.

In an embodiment, the insertion catheter may include multiple inner lumen or voids. For example, as shown in FIG. 2, the insertion catheter includes an inner void 210 for passing a light-sensitive liquid into the expandable portion and an inner lumen or a central lumen 220 for passing a light-conducting fiber (which is not illustrated in FIG. 2). The proximal end 112 of the flexible insertion catheter 101 includes at least two ports. In the embodiment shown in FIG. 1, the proximal end 112 includes three ports 115, 125, and 135. Port 115 can accept, for example, a light-conducting fiber. In an embodiment, the light-conducting fiber is an optical fiber. In an embodiment, the optical fiber has an outer diameter from about 1 mm to about 3 mm. The optical fiber is sized to pass through an inner lumen of the insertion catheter 101. The optical fiber can be made from any material, such as glass, silicon, silica glass, quartz, sapphire, plastic, combinations of materials, or any other material, and may have any diameter. In an embodiment, the optical fiber is made from a polymethyl methacrylate core with a transparent polymer cladding. It should be appreciated that the above-described characteristics and properties of the optical fibers are exemplary and not all embodiments of the present disclosure are intended to be limited in these respects. Port 125 can accept, for example, a syringe housing air or fluid. Port 135 can accept, for example, a syringe housing a light-sensitive liquid. In an embodiment, the light-sensitive liquid is a liquid monomer. In an embodiment, the syringe maintains a low pressure during the infusion and aspiration of the light-sensitive liquid. In an embodiment, the syringe maintains a low pressure of about 10 atmospheres or less during the infusion and aspiration of the light-sensitive liquid.

Light-sensitive liquid can be introduced into the proximal end 112 of the insertion catheter 101 and passes through the inner void 210 of the insertion catheter 101 up into the inner cavity 235 of the expandable portion 200 to move the expandable portion from a deflated state to an inflated state when the light-sensitive liquid is delivered to the expandable portion, in order to form a rigid orthopedic stabilizer. In an embodiment, the light-sensitive liquid is provided as a unit dose. As used herein, the term "unit dose" is intended to mean an effective amount of light sensitive liquid adequate for a single session. By way of example, a unit dose of a light sensitive liquid of the present disclosure for expanding an expandable portion of the present disclosure may be defined as enough light-sensitive liquid to expand the expandable portion so that the expanded expandable portion realigns a fractured bone and/or secures the bone back into an anatomical position. The amount of realigning may vary somewhat from user to user. Thus, a user using a unit dose may have excess light-sensitive liquid left over. It is desirable to provide enough light-sensitive liquid that even the above-average user will have an effective amount of realignment. In an embodiment, a unit dose of a light-sensitive liquid of the present disclosure is contained within a container. In an embodiment, a unit dose of a light-sensitive liquid of the present disclosure is contained in an ampoule. In an embodiment, the expandable portion is sufficiently shaped to fit within a space or a gap in a fractured bone. In an embodiment, the light-sensitive liquid can be delivered under low pressure via a standard syringe attached to the port 135. The light-sensitive liquid can be aspirated and reinfused as necessary, allowing for adjustments to the expandable portion. These properties allow a user to achieve maximum fracture reduction prior to activating a light source and converting the liquid monomer into a hard polymer.

A light-conducting fiber communicating light from the light source can be introduced into the proximal end 112 of the insertion catheter 101 through port 115 and passes within an inner lumen of the insertion catheter 101 up into the expandable portion. In an embodiment, the light source emits frequency that corresponds to a band in the vicinity of 390 nm to 770 nm, the visible spectrum. In an embodiment, the light source emits frequency that corresponds to a band in the vicinity of 410 nm to 500 nm. In an embodiment, the light source emits frequency that corresponds to a band in the vicinity of 430 nm to 450 nm. The light-sensitive liquid remains a liquid monomer until activated by the light-conducting fiber (cures on demand). In an embodiment, the liquid monomer is exposed to an appropriate frequency of light and intensity to cure the monomer inside the expandable portion and form a rigid structure. In an embodiment, the liquid monomer is exposed to electromagnetic spectrum that is visible (frequency that corresponds to a band in the vicinity of 390 nm to 770 nm). In an embodiment, the liquid monomer is radiolucent, which permit x-rays to pass through the liquid monomer. Radiant energy from the light source is absorbed and converted to chemical energy to quickly (e.g., cured in about five seconds to about five minutes) polymerize the monomer. This cure affixes the expandable portion in an expanded shape. A cure may refer to any chemical, physical, and/or mechanical transformation that allows a composition to progress from a form (e.g., flowable form) that allows it to be delivered through the inner void in the insertion catheter 101, into a more permanent (e.g., cured) form for final use in vivo. For example, "curable" may refer to uncured composition, having the potential to be cured in vivo (as by catalysis or the application of a suitable energy source), as well as to a composition in the process of curing (e.g., a composition formed at the time of delivery by the concurrent mixing of a plurality of composition components).

Additives may be included in light-sensitive liquids, including, but not limited to, drugs (for example, antibiotics), proteins (for example, growth factors) or other natural or synthetic additives (for example, radiopaque or ultrasonically active materials). In an embodiment, the viscosity of the light-sensitive liquid has a viscosity of about 1000 cP or less. In an embodiment, the light-sensitive liquid has a viscosity ranging from about 650 cP to about 450 cP. The expandable portion may be inflated, trial fit and adjusted as many times as a user wants with the light-sensitive liquid, up until the light source is activated, when the polymerization process is initiated. Because the light-sensitive liquid has a liquid consistency and is viscous, the light-sensitive liquid may be delivered using low pressure delivery and high pressure delivery is not required, but may be used.

In an embodiment, a contrast material may be added to the light-sensitive liquid without significantly increasing the viscosity. Contrast materials include, but are not limited to, barium sulfate, tantalum, or other contrast materials known in the art. The light-sensitive liquid can be introduced into the proximal end of the insertion catheter and passes within the inner void of the insertion catheter up into an inner cavity of the expandable portion to change a thickness of the expandable portion without changing a width or depth of the expandable portion. In an embodiment, the light-sensitive liquid is delivered under low pressure via the syringe attached to the port. The light-sensitive liquid can be aspirated and reinfused as necessary, allowing for thickness adjustments to the expandable body prior to activating the light source and converting the liquid monomer into a hard polymer. Low viscosity allows filling of the intramedullary implant through a very small delivery system.

One or more radiopaque markers or bands may be placed at various locations along the expandable portion 200 and/or the insertion catheter 101. A radiopaque ink bead may be placed at a distal end of the expandable portion for alignment of the apparatus during fluoroscopy. The one or more radiopaque bands and radiopaque ink bead, using radiopaque materials such as barium sulfate, tantalum, or other materials known to increase radiopacity, allows a medical professional to view the apparatus using fluoroscopy techniques. The one or more radiopaque bands also provide visibility during inflation of the expandable portion to determine the precise positioning of the expandable portion during placement and inflation. The one or more radiopaque bands permit visualization of any voids that may be created by air that gets entrapped in the expandable portion. The one or more radiopaque bands permit visualization to preclude the expandable portion from misengaging or not meeting a bone due to improper inflation to maintain a uniform expandable portion/bone interface.

In an embodiment, the expandable portion 200 can have a length greater than about 300 mm and a diameter greater than about 14 mm. In such embodiments, there is the potential that during the curing of the light-sensitive liquid, a far distal area 214 of the expandable portion 200 will exhibit a shrinkage upon cure of about 2 to about 3 percent, while a proximal area 212 of the expandable portion 200 is being cured. In an embodiment, to prevent this from transpiring, the inner lumen 220 of the expandable portion 200 can be pressurized by virtue of the infusion of either air or other fluids (saline, water) through port 125 at the proximal end 112 of the insertion catheter 101. The infusion will cause internal diameter pressure against the light-sensitive liquid contained within the inner cavity 235 of the expandable portion 200 so that during the curing process, the pressure keeps the light-sensitive liquid pressurized, and up in contact with inner surface 230 of the expandable portion 200. When the light-conducting fiber is inserted within the inner lumen 220 and the light-sensitive liquid is infused, the extra space is pressed down on the inner lumen 220. In an embodiment, an expandable portion of the present disclosure has a diameter ranging from about 4 mm to about 30 mm. In an embodiment, an expandable portion of the present disclosure has a length ranging from about 20 mm to about 300 mm. An expandable portion of the present disclosure may be round, flat, cylindrical, oval, rectangular or any desired shape for a given application. In an embodiment, an expandable portion of the present disclosure has a diameter of about 4 mm and a length of about 30 mm. In an embodiment, an expandable portion of the present disclosure has a diameter of about 5 mm and a length of about 40 mm. In an embodiment, an expandable portion of the present disclosure has a diameter of about 6 mm and a length of about 30 mm. In an embodiment, an expandable portion of the present disclosure has a diameter of about 6 mm and a length of about 40 mm. In an embodiment, an expandable portion of the present disclosure has a diameter of about 6 mm and a length of about 50 mm. In an embodiment, an expandable portion of the present disclosure has a diameter of about 7 mm and a length of about 30 mm. In an embodiment, an expandable portion of the present disclosure has a diameter of about 7 mm and a length of about 40 mm. In an embodiment, an expandable portion of the present disclosure has a diameter of about 7 mm and a length of about 50 mm.

In an embodiment, an outer surface of an expandable portion of the present disclosure is resilient. In an embodiment, an outer surface of an expandable portion of the present disclosure is substantially even and smooth. In an embodiment, an outer surface of an expandable portion of the present disclosure is not entirely smooth and may have some small bumps or convexity/concavity along the length. In an embodiment, an outer surface of an expandable portion of the present disclosure may have ribs, ridges, projections, bumps or other shapes. In an embodiment, the ribs, ridges, projections, bumps, or other shapes on the rough or uneven outer surface of the expandable portion improve penetration of the at least one fastener into the expandable portion. In an embodiment, the ribs, ridges, projections, bumps, or other shapes on the rough or uneven outer surface of the expandable portion improve penetration of the at least one fastener into the expandable portion anywhere along a length of the expandable portion. In an embodiment, the ribs, ridges, projections, bumps, or other shapes on the rough or uneven outer surface of the expandable portion increase friction between the outer surface of the expandable portion and the at least one fastener so as to reduce slippage of the at least one fastener as the at least one fastener is driven towards the outer surface of the expandable portion. In an embodiment, the ribs, ridges, projections, bumps, or other shapes on the rough or uneven outer surface of the expandable portion interacts with a threaded portion of the at least one fastener so as to improve penetration and fastening of the at least one fastener into the expandable portion. In an embodiment, the ribs, ridges, projections, bumps, or other shapes on the rough or uneven outer surface of the expandable portion interact with a tip of the at least one fastener to improve the wedge ability of the tip of the fastener so as to decrease the driving force needed to penetrate the expandable portion. In an embodiment, an outer surface of an expandable portion of the present disclosure has an uneven geometry. In an embodiment, an outer surface of an expandable portion of the present disclosure has a textured surface which provides one or more ridges that allow grabbing. In an embodiment, the one or more ridges on the textured surface of the expandable portion allow grabbing of the at least one fastener so as to improve the penetration of the at least one fastener into the expandable portion. In an embodiment, the one or more ridges on the textured surface of the expandable portion allow grabbing of bone so as to improve adhesion between the expandable portion and bone as regenerating bone grows onto the outer surface of the expandable portion. In an embodiment, abrasively treating an outer surface of an expandable portion of the present disclosure for example via chemical etching or air propelled abrasive media improves the connection and adhesion between the outer surface of the expandable portion and a bone. The surfacing may significantly increase the amount of surface area that comes in contact with the bone resulting in a stronger grip. In an embodiment, the textured surface promotes bone growth onto the expandable portion. In an embodiment, the textured surface promotes bone growth of regenerating bone onto the outer surface of the expandable portion by grabbing the regenerating bone as it grows. In an embodiment, an expandable portion of the present disclosure is made by extruding material into a tube shape, and then forming the tube into a balloon. When forming the tube into the balloon, the balloon can be, for example, pre-stamped or milled to include a desired design, desired shape or surface modification. Then, the tube is heated and radially expanded via compressed air for a specific amount of time. The formed balloon is cooled and includes the desired design, desired shape or surface modification.

In an embodiment, an expandable portion of the present disclosure has an outer surface that is coated with materials such as drugs, bone glue, proteins, growth factors, or other coatings. For example, after a minimally invasive surgical procedure an infection may develop in a patient, requiring the patient to undergo antibiotic treatment. An antibiotic drug may be added to an outer surface of an expandable portion of the present disclosure to prevent or combat a possible infection. Proteins, such as, for example, bone morphogenic protein or other growth factors have been shown to induce the formation of cartilage and bone. In an embodiment, a growth factor is added to an outer surface of an expandable portion of the present disclosure to help induce the formation of new bone. In an embodiment, as the formation of new bone is induced the new bone interacts with a textured outer surface of the expandable portion so that new bone is formed onto the textured outer surface of the expandable portion. Due to the lack of thermal egress of light-sensitive liquid in an expandable portion of the present disclosure, the effectiveness and stability of the coating is maintained.

In an embodiment, a stiffness of any of the expandable portion of the present disclosure can be increased due to the presence of external stiffening members or internal stiffening members. In an embodiment, a wrapping, sheathing or an attachment of Nitonol or other metallic memory-type metal piece(s) are aligned in a longitudinal fashion, with multiple rods being placed circumferentially around the expandable portion so as to have these metallic pieces change their configuration under a temperature change. In an embodiment, an inner surface of the metallic pieces (those surfaces that are in contact with the external circumferential surface of the intramedullary implant) are polished to increase internal reflection of the light from the light-conducting fiber. The metallic pieces are designed to be load-bearing shapes. In an embodiment, the metallic pieces have a low profile and can handle large loads. In an embodiment, metallic pieces may be positioned on the external circumferential surface of an expandable portion. The metallic pieces can be aligned in a longitudinal fashion, circumferentially around the expandable portion and can be interconnected with one another via connecting means such as wires. The wires will help hold the longitudinal metallic pieces in position. In an embodiment, the metallic pieces expand to increase the strength of the hardened expandable portion. In an embodiment, the metallic pieces contract to increase the strength of the hardened expandable portion. In an embodiment, metallic pieces are positioned on an internal circumferential surface of an expandable portion. In an embodiment, two metallic memory-type metal wires, such as nitonol, are positioned within an expandable portion. Heat from a light-conducting fiber makes the metal wires get smaller, tensioning the hardened expandable portion. In an embodiment, heat from a light-conducting fiber and reaction with the polymerization process, makes the metal wires get smaller, tensioning the hardened expandable portion. In an embodiment, an expandable portion is wrapped with a plurality of flat metallic plates that move into a corrugated or other shape upon a temperature change to increase the strength of the previously flat metal plate into a shape capable of handling a load. In an embodiment, the metals are rectangular, semicircular, hexagonal, or triangular in section, although not all embodiments are limited to these shapes.

An expandable portion typically does not have any valves. One benefit of having no valves is that the expandable portion may be inflated or deflated as much as necessary to assist in the fracture reduction and placement. Another benefit of the expandable portion having no valves is the efficacy and safety of the implant. Since there is no communication passage of light-sensitive liquid to the body there cannot be any leakage of liquid because all the liquid is contained within the expandable portion. In an embodiment, a permanent seal is created between the expandable portion that is both hardened and affixed prior to the insertion catheter 101 being removed. The expandable portion may have valves, as all of the embodiments are not intended to be limited in this manner.

In an embodiment, an expandable portion of the present disclosure includes a pathway sufficiently designed for passing a cooling medium. Once the expandable portion is expanded, a cooling media may be delivered within (via an internal lumen) or around (via external tubing) the expandable portion in order to prevent the possibility of overheating. Medium used for cooling includes, but is not limited to, gases, liquids and combinations thereof. Examples of gases include, but are not limited to, inert gases and air. Examples of liquids include, but are not limited to, water, saline, saline-ice mixtures, liquid cryogen. In an embodiment, the cooling media is water. The cooling media can be delivered to the expandable portion at room temperature or at a cooled temperature. In an embodiment, the cooling media improves the numerical aperture between that of the light-conducting fiber and the inner lumen for the light-conducting fiber because any air existing between the light-conducting fiber and the material of the expandable portion is taken away so as to improve light transmission. Therefore, the light transmission will be light-conducting fiber—cooling media—expandable portion—light-sensitive liquid as opposed to light-conducting fiber—air—expandable portion—light-sensitive liquid. In an embodiment, the cooling media transmitted through the inner lumen of the expandable portion takes away extraneous heat. In an embodiment, no cooling media is used.

In an embodiment, the inner lumen of the expandable portion penetrates through a distal end of the expandable portion for cooling through the length of the expandable portion. In an embodiment, the inner lumen has a return flow path for cooling. In an embodiment, the inner lumen is pressurized to move the cooling media in the inner lumen. In an embodiment, the expandable portion has external helical tubing for providing cooling media to the expandable portion.

In an embodiment, a light-conducting fiber can be introduced into the inner lumen of the expandable portion and activated to cure the light-sensitive liquid, while a cooling medium may flow through the inner lumen and out the distal end of the expandable portion.

FIGS. 3A-3E, in combination with FIG. 1 and FIG. 2, illustrate an embodiment of method steps for implanting an expandable portion of an intramedullary implant of the present disclosure within the intramedullary space of a weakened or fractured bone. A minimally invasive incision (not shown) is made through the skin of the patient's body to expose a fractured bone 302. The incision may be made at the proximal end or the distal end of the fractured bone 302 to expose the bone surface. Once the bone 302 is exposed, it may be necessary to retract some muscles and tissues that may be in view of the bone 302. As shown in FIG. 3A, an access hole 310 is formed in the bone by drilling or other methods known in the art. In an embodiment, the access hole 310 has a diameter of about 3 mm to about 10 mm. In an embodiment, the access hole 310 has a diameter of about 3 mm.

The access hole 310 extends through a hard compact outer layer 320 of the bone into the relatively porous inner or cancellous tissue 325. For bones with marrow, the medullary material should be cleared from the medullary cavity prior to insertion of the inventive device. Marrow is found mainly in the flat bones such as hip bone, breast bone, skull, ribs, vertebrae and shoulder blades, and in the cancellous material at the proximal ends of the long bones like the femur and humerus. Once the medullary cavity is reached, the medullary material including air, blood, fluids, fat, marrow, tissue and bone debris should be removed to form a void. The void is defined as a hollowed out space, wherein a first position defines the most distal edge of the void with relation to the penetration point on the bone, and a second position defines the most proximal edge of the void with relation to the penetration site on the bone. The bone may be hollowed out sufficiently to have the medullary material of the medullary cavity up to the cortical bone removed. There are many methods for removing the medullary material that are known in the art and within the spirit and scope on the presently disclosed embodiments. Methods include those described in U.S. Pat. No. 4,294,251 entitled "Method of Suction Lavage," U.S. Pat. No. 5,554,111 entitled "Bone Cleaning and Drying system," U.S. Pat. No. 5,707,374 entitled "Apparatus for Preparing the Medullary Cavity," U.S. Pat. No. 6,478,751 entitled "Bone Marrow Aspiration Needle," and U.S. Pat. No. 6,358,252 entitled "Apparatus for Extracting Bone Marrow."

A guidewire (not shown) may be introduced into the bone 302 via the access hole 310 and placed between bone fragments 304 and 306 of the bone 302 to cross the location of a fracture 305. The guidewire may be delivered into the lumen of the bone 302 and may cross the location of the break 305 so that the guidewire spans multiple sections of bone fragments. As shown in FIG. 3B, the expandable portion 200 of the insertion catheter 101 for repairing a fractured bone, which is constructed and arranged to accommodate the guidewire, is delivered over the guidewire to the site of the fracture 305 and spans the bone fragments 304 and 306 of the bone 302. Once the expandable portion 200 is in place, the guidewire may be removed. The location of the expandable portion 200 may be determined using at least one radiopaque marker 330 which is detectable from the outside or the inside of the bone 302. Once the expandable portion 200 is in the correct position within the fractured bone 302, a delivery system which contains a light-sensitive liquid is attached to the port 135. The light-sensitive liquid is then infused through the inner void 210 in the delivery catheter 101 and enters the inner cavity 235 of the expandable portion 200. This addition of the light-sensitive liquid within the expandable portion 200 causes the expandable portion 200 to expand, as shown in FIG. 3C. As the expandable portion 200 is expanded, the fracture 305 is reduced. Unlike traditional implants, such as rods, that span the fracture site, the expandable portion 200 of the present disclosure does more than provide longitudinal strength to both sides of the fractured bone. In an embodiment, the expandable portion 200 having the design can be a spacer for reducing the fracture and for holding the fractured and compressed bones apart at the point of the collapsed fracture.

Once orientation of the bone fragments 304 and 306 are confirmed to be in a desired position, the light-sensitive liquid may be hardened within the expandable portion 200, as shown in FIG. 3D, such as by illumination with a visible emitting light source. In an embodiment, during the curing step, a syringe housing a cooling media may be attached to the proximal end of the insertion catheter and continuously delivered to the expandable portion 200. The cooling media can be collected by connecting tubing to the distal end of the inner lumen and collecting the cooling media via the second distal access hole. After the light-sensitive liquid has been hardened, the light source may be removed from the device. Alternatively, the light source may remain in the expandable portion 200 to provide increased rigidity. The expandable portion 200 once hardened, may be released from the delivery catheter 101 by known methods in the art. As shown in FIG. 3E, the hardened expandable portion remains in the fractured bone, and the insertion catheter is removed. In an embodiment, each surface of the expandable portion may be in contact with the bone. In an embodiment, at least a portion of a surface of the expandable portion may be in contact with the bone.

An implant may need to be removed for a number of reasons, including, but not limited to situations where an implant is rejected, an infection develops, the bone is healed, the implant is technologically outdated, or if the implant is defective or otherwise not placed properly. Conventional techniques of removing implants may break the implant causing it to harm the surrounding bone or may result in infection of the bone. Implant removal systems that remove implants from bones using minimally invasive techniques, with ease of use, and minimal damage to the bone and supporting tissues are desired.

In an embodiment, the devices, systems and kits disclosed herein act as implant removal systems for removing implants from fractured bones. In an embodiment, the system of the present disclosure includes a wire, having a distal end, a toggle configured to move about a hinge from a first position to a second position and back again, and a plurality of burrs configured to be positioned over longitudinal axis of the wire, wherein the plurality of burrs have incrementally increasing diameters for removing portions of the implant.

Figure 4:
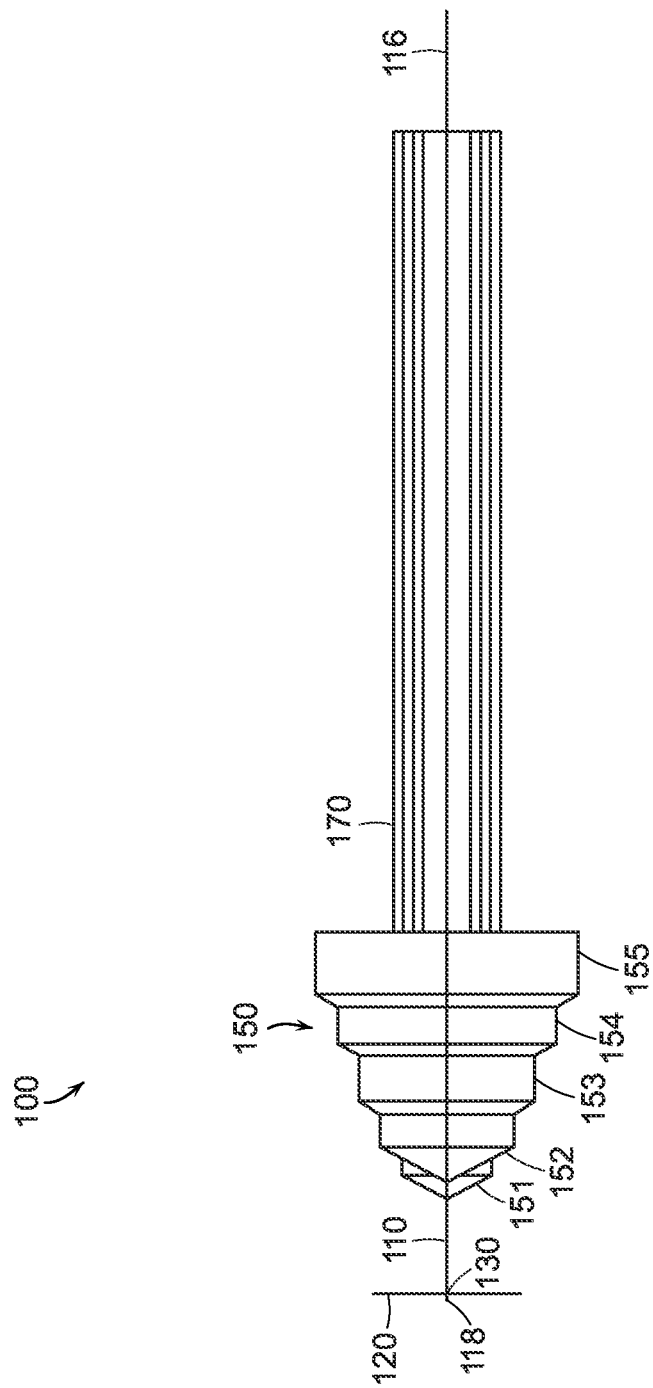
FIG. 4 shows a burr component of an embodiment of an implant removal system of the present disclosure.

In an embodiment, an implant removal system 100 of the present disclosure is illustrated in FIG. 4. As shown in FIG. 4, the implant removal system 100 may include a wire 110 used to guide the implant removal system 100 through an implant to be removed (not shown). The wire 110 includes a proximal end 116 and a distal end 118. In an embodiment, the wire 110 can be made from a substantially flexible material. In an embodiment, the wire 110 can be made from a substantially hard material. In an embodiment, the wire 110 is hollow. In an embodiment, the wire 110 is substantially solid. In an embodiment, the material used to make the wire can have properties including, but not limited to, low density, high strength, corrosion resistance, shape memory, superelasticity, or combinations thereof. Examples of materials from which the wire 110 can be made from include, but are not limited to, metal, plastic, alloys, or any other material known in the art. In an embodiment, the wire 110 can be composed of a medical grade material. Examples of medical grade materials include, but are not limited to, stainless steel, titanium, nickel titanium, nickel titanium alloy, alloys, combinations thereof, or any other similar materials. The material chosen for the wire 110 is dependent on a variety of factors, including, but not limited to, the length of the implant, the density of the implant, and the location of the implant.

In an embodiment, the wire 110 has a diameter large enough for the wire to retain its structural integrity while being guided through the implant. In an embodiment, the wire 110 has a diameter sufficiently large to receive enough force to guide the wire through the implant along the entire length of the implant without the wire deforming in a manner that will prevent the wire from reaching the end of the implant. In an embodiment, the wire 110 has a diameter ranging from about 0.015 mm to about 0.05 mm. In an embodiment, the wire 110 has a diameter ranging from about 0.028 mm to about 0.040 mm. In an embodiment, the wire 110 can be of any length desired so long as the length allows the wire to travel through the entire length of the implant and extend past a distal end of the implant.

In an embodiment, an implant removal system 100 of the present disclosure may be utilized to remove an implant having a central lumen. In such embodiments, the wire 110 has a diameter sufficiently sized to allow the wire 110 to fit through the central lumen of the implant. In an embodiment, the outer diameter of the wire is only slightly smaller than the inner diameter of the central lumen, which will aid the user in centering the implant removal system 100 relative to the implant.

At the distal end 118, a toggle 120 is hingedly coupled to the wire 110. In an embodiment, the toggle 120 can pivot from about 0 degrees to about 180 degrees in relation to the wire 110. In an embodiment, the toggle 120 can pivot from about 0 degrees to about 360 degrees in relation to the wire 110. In an embodiment, a hinge 130 is disposed at the point where the wire 110 and toggle 120 are coupled.

FIG. 5A shows the toggle 120 in a first position, or closed position. In the first position, the toggle 120 is in substantial axial alignment with the wire 110 as well as the implant to allow the toggle 120 to travel through the implant. In an embodiment, the toggle 120 can be composed of a medical grade material. In an embodiment, the material used to make the toggle 120 can have properties including, but not limited to, low density, high strength, corrosion resistance, shape memory, superelasticity, chemical inertness, or combinations thereof. In an embodiment, the toggle 120 can be composed of a medical grade material. Examples of medical grade materials include, but are not limited to stainless steel, titanium, nickel titanium, nickel titanium alloy, alloys, combinations thereof, or any other similar materials. Radiopacifying agents are often added to medical devices components to enhance the visibility of the component in radiography. In an embodiment, a radiopacifying agent can be applied to the toggle 120 to confer radiopacity to the toggle to increase the visibility of the toggle 120 during radiography. In an embodiment, the radiopacifying agent comprises tantalum.

FIG. 5B shows the toggle 120 in a substantially second position, or partially open position. In the second position, the toggle 120 is pivoted approximately 90 degrees on the hinge 130 to form a substantially t-shaped design and be substantially perpendicular to the implant. In an embodiment, the toggle 120 is pivoted approximately 90 degrees. In this open position, the toggle 120 is designed to stabilize or lock the implant removal system 100 in position within the implant. When the toggle 120 is in the second position, the wire 110 can be pulled to move or resituate the implant, which is held by the toggle 120. Such movement may be desirable, for instance, to move the implant closer to the user or to align the implant with the user.

In an embodiment, the toggle 120 is designed to switch from a first to a second position and from a second to a first position through the use of a weight (not shown) associated with the toggle 120. In an embodiment, the weight is situated on one side of the toggle 120. In an embodiment, the weight is designed to maintain a balance such that when the weight senses that there is little or no support underneath, the weight pushes the toggle 120 forward, causing the toggle 120 to switch from a closed to an open position. Similarly, when the weight encounters more resistance underneath, the weight pushes the toggle 120 upward, causing the toggle 120 to switch from an open to a closed position. It should be noted that the weight can be any desired shape or size as long as the weight can be associated with the toggle 120.

In an embodiment, the toggle 120 has a substantially rectangular shape. In an embodiment, the toggle 120 has a square, triangular, pentagonal, or any other geographic shape desired. In an embodiment, the toggle 120 has any width, thickness or length desired so long as the toggle 120 can travel through the central lumen of the implant in its closed position.

Referring back to FIG. 4, the implant removal system of the present disclosure includes a plurality of burrs, shown generally as 150, designed to remove, core out or ream out portions of the implant. Although in the embodiment illustrated in FIG. 4, the plurality of burrs 150 includes five burrs 151, 152, 153, 154, and 155, the number of burrs may vary as necessary or desired. In an embodiment, the burrs 150 may act as a drill to drill out portions of the implant. In an embodiment, each of the plurality of burrs 150 can be customized to remove an implant without causing damage to bone adjacent the implant. In an embodiment, each of the plurality of burrs 150 can be designed to be sequentially larger for progressive removal of the implant without causing damage to bone adjacent to the implant. In an embodiment, each of the plurality of burrs 150 can be selected to have a different shape to allow removal of an implant without the burrs 150 contacting bone adjacent to the implant. In an embodiment, each of the plurality of burrs 150 can be selected to have a diameter that will allow the burrs 150 to remove portions of the implant without engaging bone adjacent to the portions of the implant to be removed. In an embodiment, each of the plurality of burrs 150 are selected as a series of burrs 150 to approximately match the contours of a portion of an implant to be removed without damaging bone adjacent to the portion of the implant. In an embodiment, each of the plurality of burrs 150 can be selected during an implant removal treatment based on observations of the implant to be removed during the treatment.

Figure 6:
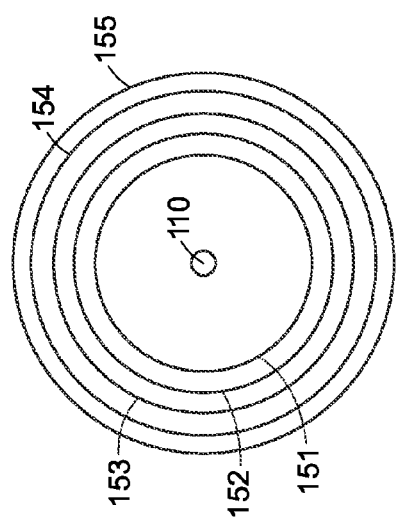
FIG. 6 shows a front plan view of an embodiment of the system of the present disclosure.

In an embodiment, the burrs 150 are designed to be of increasing size such that each subsequent burr is larger than the previous burr. In an embodiment, a first burr 151 is followed by a second burr 152 larger than the first burr, which is followed by a third burr 153 larger than the second burr, followed by as many burrs 150 as desired, which are each larger than the previous burrs 150. In an embodiment, the burrs 150 are designed to be of decreasing size such that each subsequent burr is smaller than the previous burr. In an embodiment, a first burr is followed by a second burr smaller than the first burr, which is followed by a third burr smaller than the second burr, followed by as many burrs as desired, which are each smaller than the previous burrs. For example, FIG. 4 illustrates an embodiment with five burrs 151-155 of increasing size and FIG. 6 illustrates a front plan view of these burrs. It should be appreciated that the burrs do not have to be in either increasing or decreasing order. In an embodiment, the burrs are designed to be of varying sizes independently of other burrs.

In an embodiment where an implant removal system of the present disclosure is utilized to remove an implant having a central lumen, the diameter of the burrs 150 can be designed to be larger than the diameter of the lumen of the implant. In an embodiment, each of the plurality of burrs 150 selected to remove a portion of an implant having a central lumen can be chosen such that all burrs 150 have a diameter larger than the diameter of the central lumen of the implant to keep the burrs 150 centered while removing the implant. Moreover, selecting a wire with an outer diameter only slightly smaller than the inner diameter of the central lumen will also aid in centering the implant removal system 100.

In an embodiment, each subsequent burr used to remove an implant is designed to be larger than the previous burr to increase the diameter of the lumen of the implant in a progressive manner until the implant is substantially removed. In an embodiment, the diameter of the burrs 150 can range from about 1 mm to about 10 mm in size. In an embodiment, the diameter of the burrs 150 can range from about at least about 1.5 mm to at least about 2 mm. In an embodiment, the diameter change between adjacent burrs 150 can range from about 0.25 mm to about 1.5 mm. In an embodiment, the diameter change between adjacent burrs 150 can range from about 1 mm to about 2 mm. The physical characteristics, including, the density, hardness, diameter, and shape of the implant to be removed play a role in choosing the desired diameter of a burr or the diameter changes between adjacent burrs 150.

In accordance with the present disclosure, a plurality of burrs may be inserted to core or drill out the implant. In an embodiment, a first burr is designed to drill or cut through a portion of the implant surrounding the wire 110. The first burr moves through substantially the entire length of the implant and terminates at the distal end 118 of the wire 110 adjacent the toggle 120. In an embodiment, the first burr penetrates through the implant. In an embodiment, each subsequent burr that is employed in connection with the implant removal system 100 of the present disclosure is designed to core or remove an additional portion of the implant. Each subsequent burr is designed to move through the length of the implant and terminate at the previous burr to form a substantially conical shape. In an embodiment, each subsequent burr is designed to move and drill through substantially the entire length of the implant. In an embodiment, each subsequent burr is designed to move and drill through substantially the entire length of the implant and beyond. In an embodiment, the plurality of burrs 150 are designed to penetrate beyond the entire length of the implant to remove substantially all of the implant. In an embodiment, the each subsequent burr may penetrate through the implant. As each subsequent burr approaches the distal end 118 of the wire 110, the burrs may stack on top of one another. Alternatively, as each subsequent burr approaches the distal end 118 of the wire 110, the burrs may push one another forward.

Figure 7A:
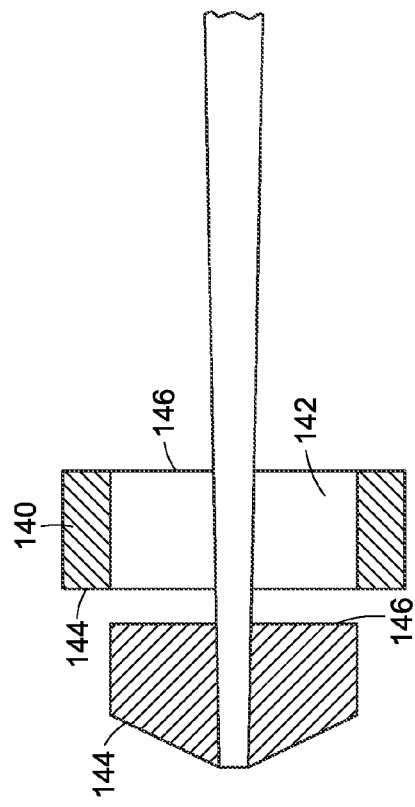
FIG. 7A and FIG. 7B show burr components of an embodiment of the system of FIG. 1.

Referring to FIG. 7A, in an embodiment, each burr includes a distal face 144 and an opposing proximal face 146. In an embodiment, the distal face is rough or jagged to allow a burr to drill or cut through a portion of the implant. In an embodiment, the distal face approximates a conical shape. In an embodiment, the distal face is flat. It should be noted the distal face may have other geometric shapes as well. In an embodiment, the proximal face is smooth. In an embodiment, the proximal face is rough. In an embodiment, the first burr may have a conical distal face and a flat proximal face and each subsequent burr may include two substantially flat faces to allow the burrs to align themselves adjacent to one another forming a substantially conical shape. Of course, it should be appreciated that the faces of adjacent burrs need not necessarily be flat. In an embodiment, each burr has a distal face approximating a conical shape. In an embodiment, each burr has either a conical distal end, a flat distal end, or a distal end approximating other geometric shapes independently of other burrs. In one embodiment, the adjacent faces may have a convex shape. In one embodiment, the adjacent faces may have a concave shape. The adjacent faces can have any other shape known in the art as long as the shapes allow the faces of adjacent burrs to conform to one another.

Figure 7B:
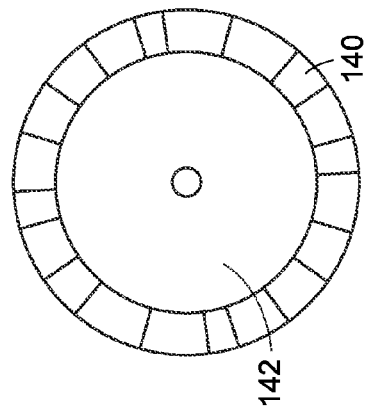

In an embodiment, each burr may include a cutting portion 140 and a non-cutting portion 142, as illustrated in FIG. 7A and FIG. 7B. In an embodiment, the cutting portion 140 may be rough to allow the cutting portion to drill or cut through the implant. As shown in FIG. 7A and FIG. 7B, the cutting portion 140 may be situated at or near the edges of the burrs and the non-cutting portion 142 may be situated in between the cutting portions 140. In an embodiment, the cutting portion 140 circumferentially surrounds the non-cutting portion 142. In an embodiment, the cutting portion 140 may cover a distal face of a burr, the edges of a burr, or both.

The cutting portion 140 allows the burrs 150 to cut or core out a portion of the implant beyond that which was cut by the previous burr. For example, if one burr has a diameter of about 3 mm, and the proximally adjacent burr has a diameter of about 3.5 mm, the overlapping area of the burrs 150 would be the non-cutting portion 142 and the extra area of the second burr would be the cutting portion 140. In this scenario, the adjacent burr would remove the portion of the implant that extends beyond the area of the previous burr. It should also be appreciated that the cutting portion 140 may cover the entirety of the burrs 150, may cover only the outer edges of the burrs 150, or may cover any portion of the area in between In an embodiment, the non-cutting portion 142 may be hollow. In an embodiment, the non-cutting portion 142 may be substantially smooth to allow the non-cutting portion 142 to reduce or eliminate friction between adjacent burrs 150. In an embodiment, the non-cutting portion 142 may include a coating designed to reduce or eliminate friction between adjacent burrs 150. In an embodiment, the material used for coating the non-cutting portion 142 can have properties including, but not limited to, reduced friction, abrasion resistance, good release, chemical resistance, and biocompatibility. Examples of materials suitable for coating the non-cutting portion include, but are not limited to, polytetrafluoroethylene, fluorinated ethylene propylene, Teflon®, Xylan®, or other similar materials.

FIG. 8 shows an embodiment of the implant removal system 100 of the present invention with five burrs 152, 156, 158, 160 and 162. In an embodiment, a first burr 152 includes a conical-shaped face and each subsequent burr 156, 158, 160 and 162 includes a frustoconical shaped face. In an embodiment, each subsequent burr 156, 158, 160 and 162 has a rough cutting portion 155 and a smooth non-cutting portion 157. In an embodiment, the first burr 152 has a diameter ranging from about 2 mm to about 3.5 mm. In an embodiment, a second burr 156 has a diameter ranging from about 3.0 mm to about 3.7. In an embodiment, a third burr 158 has a diameter ranging from about 3.5 mm to about 4.0 mm. In an embodiment, a fourth burr 160 has a diameter ranging from about 3.7 mm to about 4.5 mm. In an embodiment, a fifth burr 162 has a diameter ranging from about 4.0 mm to about 5.0. Although shown with five burrs 150, it should be appreciated that the implant removal system 100 can have more or fewer burrs 150 and still remain within the spirit and scope of the present invention.

Figure 9B:
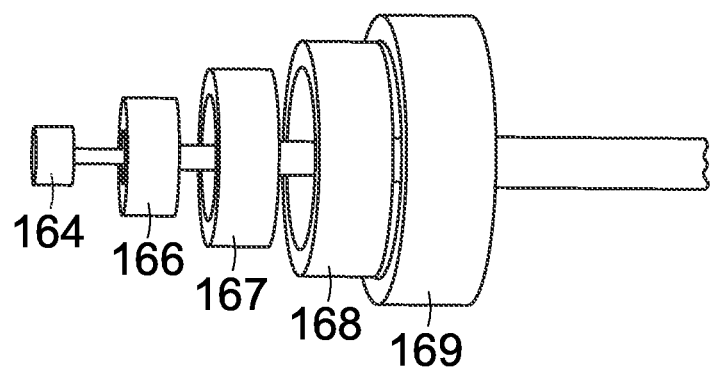
Figure 9C:
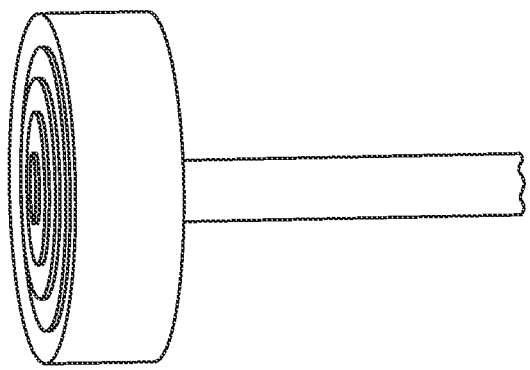

FIG. 9A, FIG. 9B, and FIG. 9C show an embodiment of the implant removal system 100 of the present invention with five burrs 164, 166, 167, 168, 169. In an embodiment, each of the burrs 164, 166, 167, 168, 169 has a flat face. In an embodiment, each of the burrs 164, 166, 167, 168, 169 are circular in shape. In an embodiment, second burr 166, third burr 167, fourth burr 168, and fifth burr 169 each have a rough cutting portion 165 and a hollow non-cutting portion 161. In an embodiment, the first burr 164 has a diameter ranging from about 2 mm to about 3.5 mm. In an embodiment, a second burr 166 has a diameter ranging from about 3.0 mm to about 3.7. In an embodiment, a third burr 167 has a diameter ranging from about 3.5 mm to about 4.0 mm. In an embodiment, a fourth burr 168 has a diameter ranging from about 3.7 mm to about 4.5 mm. In an embodiment, a fifth burr 169 has a diameter ranging from about 4.0 mm to about 5.0. Although shown with five burrs 150, it should be appreciated that the implant removal system 100 can have more or fewer burrs and still remain within the spirit and scope of the present invention.

As shown in FIG. 9A, FIG. 9B, and FIG. 9C, in an embodiment, second burr 166, third burr 167, fourth burr 168, and fifth burr 169 each have a hollow portion 161 in order to allow these burrs to slide over a preceding burr, i.e. to stack the burrs over one another as shown in FIG. 9C. In an embodiment, the inner diameter of a hollow section of a burr is the same or slightly larger than the outside diameter of the immediately preceding burr. In such embodiments, all burrs can travel the entire length of the implant to the distal end of the wire.

In accordance with an embodiment of the present invention, the burrs 150 can be made from a material that is sufficiently hard to allow the burrs 150 to drill through an implant. The burrs 150 can be made from materials having properties including, but not limited to, high tensile strength, stiff, hard, chemical resistant, or other similar properties.

Examples of materials from which the burrs 150 can be made from include, but are not limited to, metal, plastic, stainless steel, alloys, ceramics, polyetherimide, polyvinylidene fluoride, or any other material known in the art. The material chosen for the burrs 150 is dependent on a variety of factors, including, for example, the physical characteristics of the implant, or the size of each subsequent burr to be used for removing the implant.

In an embodiment, the burrs 150 have any thickness or width desired so long as the burrs 150 can travel through the implant. In an embodiment, the burrs 150 are sufficiently sized to travel through the implant without engaging the surrounding bone. In an embodiment, the burrs 150 can have any geometric shape desired so long as the burrs 150 can move through the implant. In an embodiment, the burrs 150 may have a conical shape or a frustoconical, as shown in FIG. 8. In an embodiment, the burrs 150 may have a circular shape, as shown in FIGS. 9A-9C. Although FIG. 8 and FIGS. 9A-9C illustrate the burrs 150 as being conical or circular in shape, it should be appreciated that the burrs 150 can also be triangular, square, pentagonal, hexagonal, or any other geometric shape.

Referring again to FIG. 4, each burr of the plurality of burrs 150 may be coupled to a shaft of a plurality of shafts 170 designed to guide each burr 150 through the implant. In an embodiment, the shafts 170 are designed to be of increasing size such that each subsequent shaft is larger than a previous shaft. In an embodiment, the shafts can be made from a substantially flexible material. In an embodiment, the shafts can be made from a substantially hard material. In an embodiment, the shafts are hollow to allow the shafts to be positioned or stacked over one another. Examples of materials from which the shafts can be made from include, but are not limited to, metal, plastic, stainless steel, alloys, or any other material known in the art. The material chosen for a shaft is dependent on a variety of factors, including the length of the implant needed to travel through, the density of the implant, and the location of the implant.

In an embodiment, to remove an implant in practice, the medical professional makes an incision through the skin to expose the bone. Once the bone is exposed, it may be necessary to retract some muscles and tissues that may be in view of the bone. If the implant is an intramedullary implant, penetration through the compact layer (cortical bone), the spongy layer (cancellous bone) and a portion of the medullary cavity of the bone may be accomplished by any method known in the art and be within the spirit and scope of the presently disclosed embodiments.

Implant removal may be done without any visualization of the process or using various medical imaging techniques. Suitable medical imaging techniques for monitoring implant removal include, but are not limited to, x-ray, fluoroscopy, magnetic resonance imaging (MRI), ultrasound imaging, Fourier transform infrared spectroscopy, ultraviolet or visible spectroscopy.

Once the bone is exposed, it may be necessary to access the implant situated within the bone. The access hole may be a minor drill hole with a diameter of about 3 mm to about 10 mm. A bone drill, awl or other medical device is used to gain access through the compact layer, the spongy layer and a portion of the medullary cavity. The location of the bone penetration site may be proximal or distal to the location of the weakened or fractured bone. In using a drill bit, it is desirable for the drill bit to be applied at an angle other than about 90° to the bone, for example, at an angle of about 20 degrees to about 45 degrees. The drill bit may be aimed toward the crack line of the weakened area in the bone.

Figure 10A:
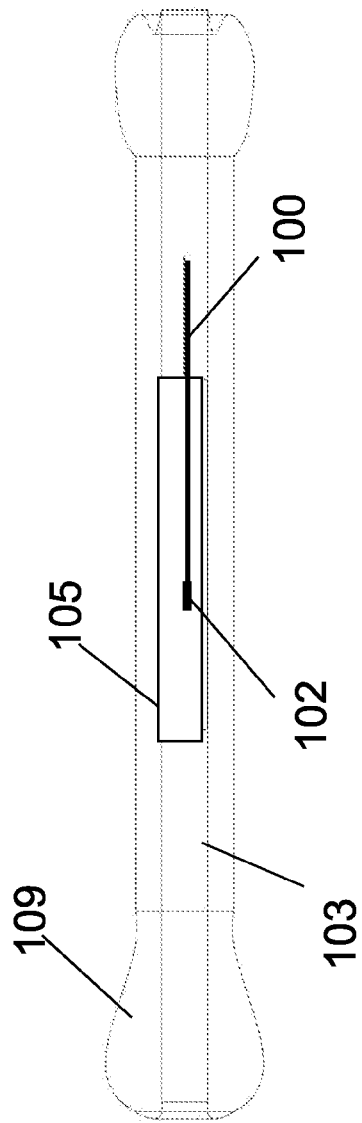
Figure 10B:
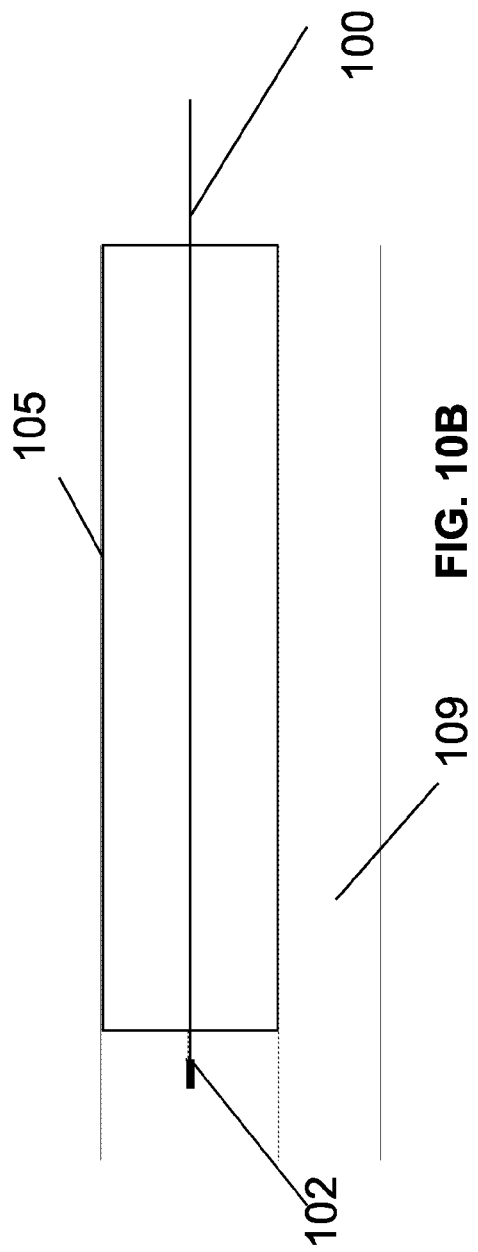

Once the implant is located and exposed, removal of the implant may occur. FIGS. 10A-10F show an embodiment of method steps for removal of an intramedullary implant using an implant removal system of the present disclosure. In an embodiment, a system for implant removal includes a wire 100 having at its distal end a toggle 102. The wire 100 is inserted through the center of the implant 105 located in a medullary cavity 103 of a bone 109, as shown in FIG. 10A. As the toggle 102 passes through the center of the implant 105, the toggle 102 is in a first position. In an embodiment, a hole or a lumen may be drilled through the implant 105 in order to facilitate insertion of the wire 100 therethrough. Once the toggle 102 reaches the distal end 107 of the implant 105, the toggle 102 switches from the first position, as shown in FIG. 10B, to a second position, as shown in FIG. 10C. In this second position, the toggle 102 acts to lock or stabilize the removal system 100 in place. FIG. 10D shows a side view of a first burr 104 being delivered over the wire 100 and through the implant 105. The first burr 104 travels through the implant 105 to the distal end 107 of the implant 105 and removes a section of the implant 105 in the middle of the implant around the wire 110. FIG. 10E shows a side view of a second burr 106 being delivered through the implant 105. The second burr 106 is larger in diameter than the first burr 104 and drills through an additional portion of the implant 105 surrounding the area that was removed by the first burr 104. The second burr 106 travels through the implant 105 and aligns itself adjacent to the first burr 104. FIG. 10F shows a side view of a third burr 108 being delivered through the implant 105. The third burr 108 is larger in diameter than both the first burr 104 and second burr 106 and drills through an additional portion of the implant 105 surrounding the area that was removed by the first burr 104 and second burr 106. The third burr 108 travels through the implant 105 and aligns itself adjacent to the second burr 106 at the distal end 107 of the implant 105. Additional burrs can be inserted until the implant 105 is substantially removed. It should be appreciated that while the burrs are driven to beyond the end of the implant 105 to substantially remove the implant 105, remaining debris from the implant may be observed. Remaining debris from the implant 105 may be washed out, scraped or removed according to methods known in the art.

FIGS. 11A-11J illustrate method steps of the presently disclosed embodiments used for removing an implant 85 having a central lumen 82 from within a bone 80. Once the central lumen of the implant is located and exposed, removal of the implant may occur. Referring to FIG. 11A and FIG. 11B, a wire 90, having at its distal end a toggle 92, is inserted into the central lumen 82 of the implant 85, which aids in centering the implant removal system relative to the implant. As the toggle 92 passes through the central lumen 82 of the implant 85, the toggle 92 is in a first position. Once the toggle 92 reaches the distal end 87 of the implant 85, the toggle 92 switches to a second position, as shown in FIG. 11C and FIG. 11D. In this second position, the toggle 92 acts to lock or stabilize the implant 85 in place. FIG. 11E and FIG. 11F show a side view of a first burr 94 being delivered over the wire 90 and through the implant 85. The first burr 94 travels through the implant 85 to the distal end 87 of the implant 85 and removes a section of the implant 85 around the central lumen 82. FIG. 11G and FIG. 11H show a side view of a second burr 96 being delivered through the implant. The second burr 96 is larger in diameter than the first burr 94 and drills through an additional portion of the implant 85 surrounding the area that was removed by the first burr 94. The second burr 96 travels through the implant 85 and aligns itself adjacent to the first burr 94. FIG. 11I and FIG. 11J show a side view of a third burr 98 being delivered through the implant. The third burr 98 is larger in diameter than both the first burr 94 and second burr 96 and drills through an additional portion of the implant 85 surrounding the area that was removed by the first burr 94 and second burr 96. The third burr 98 travels through the implant 85 and aligns itself adjacent to the second burr 96 at the distal end 87 of the implant 85. Additional burrs can be inserted until the implant 85 is substantially removed.

It should be appreciated that while the burrs are driven to beyond the end of the implant to substantially remove the implant, remaining debris from the implant may be observed. Remaining debris from the implant may be washed out, suctioned out or scraped or removed according to methods known in the art.

Figure 12:
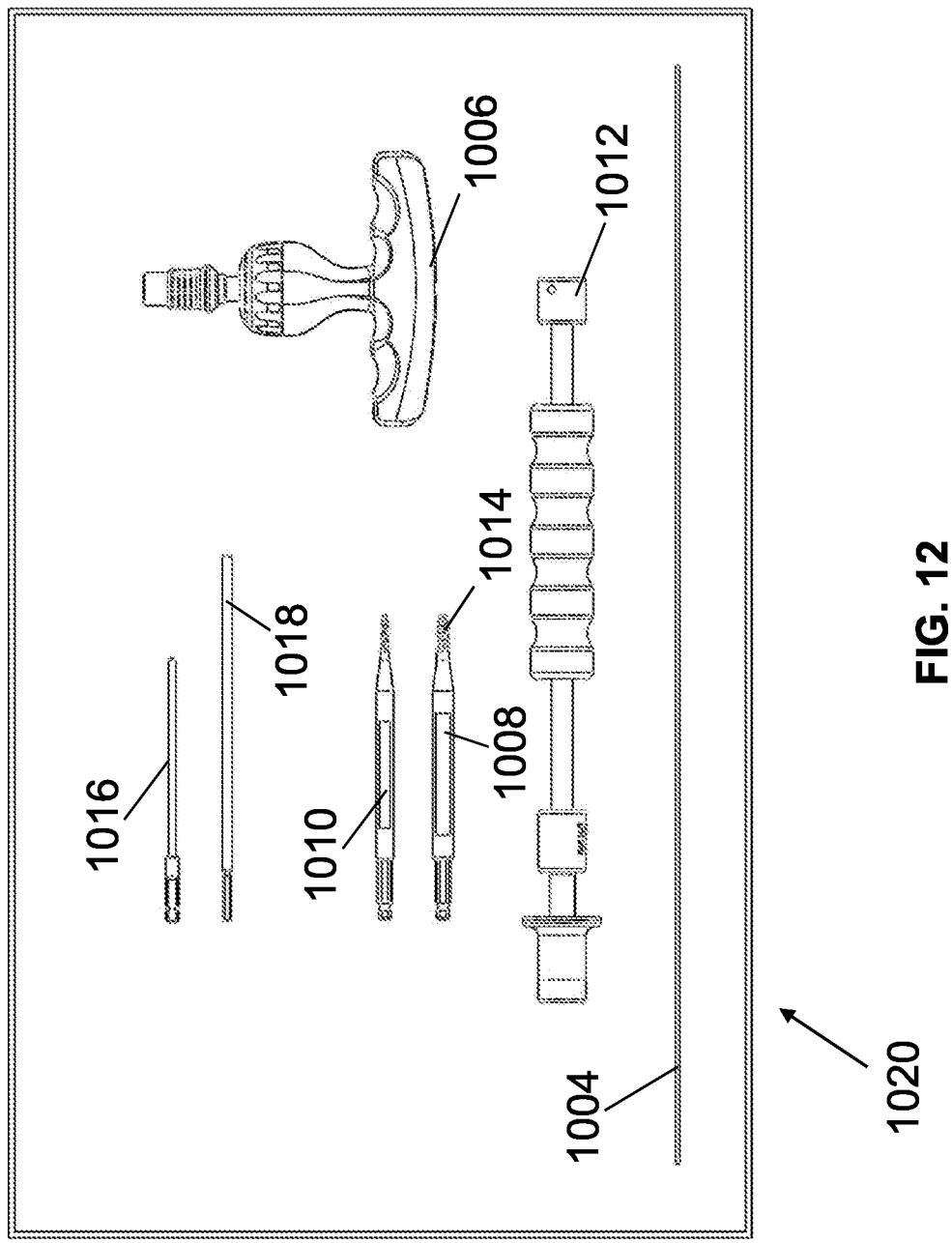
FIG. 12 shows an embodiment of a kit of the present disclosure for removal of an intramedullary device from a bone.

In an embodiment, a system or kit 1020 for removal of an implant 1000 formed of a hardened light sensitive liquid from an intramedullary cavity of a bone 1002 is provided. As shown in FIG. 12, the kit 1020 includes one or more removal screws 1008, one or more guidewires 1004, one or more drill bits 1016, a ratcheting handle or ratchets 1006, and a slaphammer 1012. The removal screws 1008, guidewires 1004, and drill bits 1016 may be of various diameters or sizes to accommodate implants 1000 of different sizes. In an embodiment, the kit 1020 may include at least one cannulated removal screw 1008 and at least one non-cannulated screw 1010. In an embodiment, the guidewires 1004 are selected such that the guidewires 1004 can be received through the cannulated removal screws 1008 to allow the cannulated removal screw 1008 to be advanced to the implant 1000 and threaded into the implant 1000 over the guidewires 1004. In an embodiment, at least one of the guidewires 1004 is a ball tipped guidewire. The ball at the tip of the guidewire 1004 decreases friction as the guidewire 1004 is passed through the central lumen. In addition, the ball at the tip of the guidewire 1004 may assist the user to retrieve any bone or implant fragments generated during the removal of the implant 1000. The removal screws 1008 are threaded at the distal tip. In an embodiment, the thread 1014 is designed to mate the removal screw 1008 to the implant 1000 and for pullout strength in the implant 1000. In an embodiment, the thread 1014 has pitch, root and major diameters and length sized to facilitate an easy insertion of the removal screw into the implant 1000. The thread 1014 is also designed to create a pullout interface, i.e. an engagement between the removal screw and the implant, capable of withstanding forces that exceed the resistance force on the implant 1000 due to friction with the walls of the bone and/or tissue adhesions as the implant 1000 is removed from the intramedullary cavity, without damaging the implant, i.e. stripping of the implant. The slaphammer 1012 and the removal screws 1008 are provided with corresponding quick connect features to facilitate their coupling. In an embodiment, the removal screws snap in, interlock or has other mechanical connection to engage the slaphammer 1012. The ratchet handle 1006 and the removal screws 1008 are provided with corresponding quick connect features to facilitate their coupling. In an embodiment, the removal screws snap in, interlock or has other mechanical connection to engage the ratchet handle 1006. In an embodiment, the ratcheting handle 1006 can also be cannulated to allow the ratcheting handle 1006 to slide over a guidewire 1004. In an embodiment, the weight and size of the slaphammer 1012 are optimized to apply sufficient amount of force to remove the implant 1000, without pulling out the removal screw 1008 from the implant 1000 or otherwise damaging the implant 1000. In an embodiment, the slaphammer is cannulated. In an embodiment, the kit 1020 includes one or more cannulated drill bits 1016, one or more non-cannulated drill bits 1018, or both. In an embodiment, the drill bits 1016, 1018 are utilized to create pilot lumens for the guidewire 1004 to be inserted into the implant 1000. The drill bits 1016, 1018 can also be used to create pilot lumens for the insertion of the removal screws 1008 to ensure full thread purchase and to prevent splitting or bulging of the implant 1000 adjacent to the interface with the removal screw 1008.

In an embodiment, as shown in FIGS. 13A-13G, a method for the removal of the implant 1000 from the intramedullary cavity of the bone 1002 using the tools of the kit 1020 is provided. After access to the implant 1000 inside the intramedullary cavity of the bone 1002 has been gained, a removal screw 1008 can be threaded into the implant 1000. In an embodiment, the removal screw 1008 is threaded into the implant 1000 with a ratcheting T handle 1006.

Figure 13A:
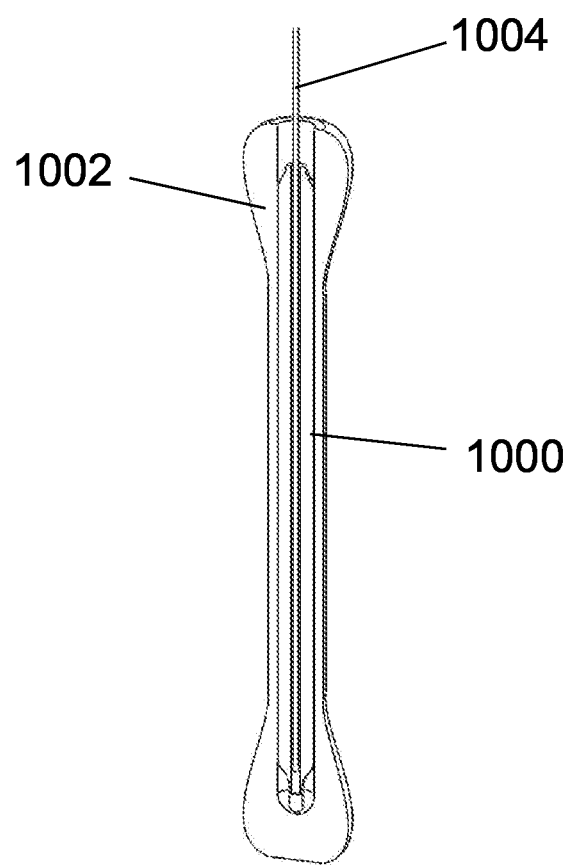
FIGS. 13A-13G show an embodiment of method steps for removing an intramedullary device from a bone using the embodiment kit of FIG. 12.

In an embodiment, a guidewire 1004 is first inserted into the implant 1000, as shown in FIG. 13A. In an embodiment, the guidewire 1004 may be inserted into a pre-existing lumen of the implant 1000. The term "pre-existing lumen" refers to a lumen that already exists in the implant as implanted, i.e., before the commencement of the removal procedure. For example, the inner lumen or central lumen 220 of the expandable portion 200 is a pre-existing lumen. In an embodiment, the guidewire 1004 may be inserted into the central lumen of the implant 1000, such that the guidewire 1004 passes substantially through the center of the implant 1000. In an embodiment, the implant 1000 may be asymmetric relative to the central lumen, for example due to the natural curvature of the intramedullary cavity of the bone 1002, in which instance, a drill may be used to create a new lumen in the implant 1000 so that the guidewire 1004, when inserted into the newly-drilled lumen, passes substantially through the center of the implant 1000. It should be noted that when the guidewire 1004 is inserted into the central lumen, the central lumen may also require preparation with a drill before the guidewire 1004 can be inserted into the central lumen. In an embodiment, drills bits 1016, 1018 are used to remove material at the proximal end of the implant 1000 surrounding or in proximity of the central lumen to prevent splitting or "flowering" of the implant 1000 during insertion of the removal screw 1008. In an embodiment, the cannulated drill bit 1016 is attached to a power or hand drill and is advanced over the guidewire into the implant 1000, approximately 1 cm to 3 cm or as necessary to remove sufficient implant material.

Figure 13B:
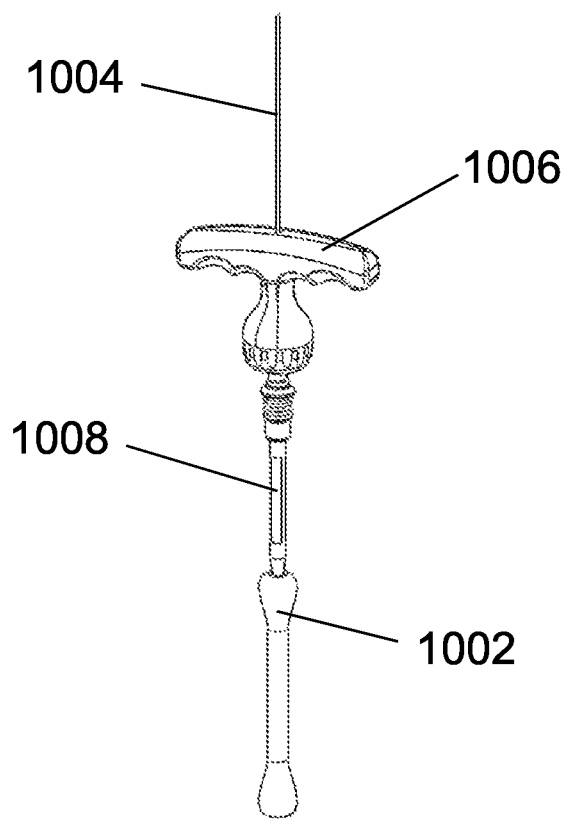
Figure 13C:
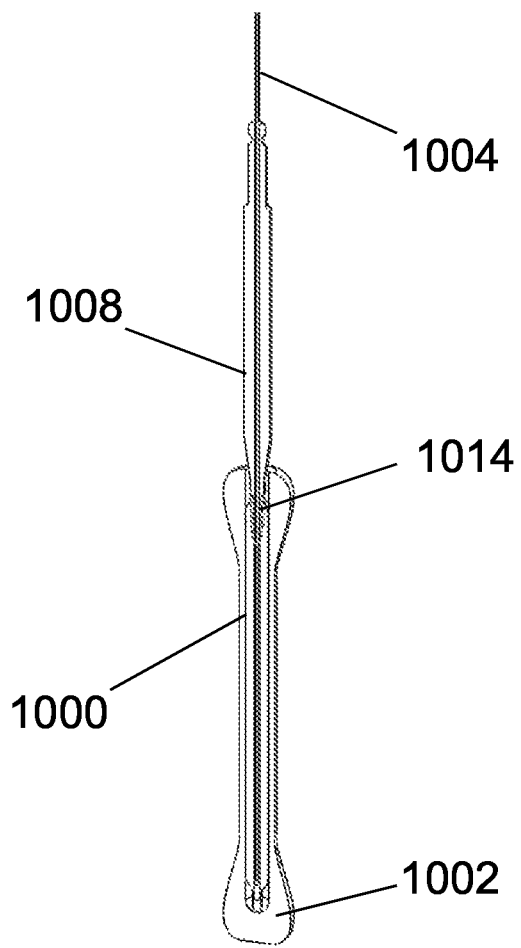

As shown in FIG. 13B and FIG. 13C, once the guidewire 1004 is placed into the implant 1000, a cannulated removal screw 1008 may be advanced over the guidewire 1004 and threaded into the implant 1000. Because the cannulated removal screw 1008 is advanced over the guidewire 1004 placed into the implant 1000, the cannulated removal screw 1008 is substantially centered relative to the implant 1004.

In an embodiment, a non-cannulated removal screw 1010 may be utilized. In such an embodiment, the non-cannulated removal screw 1010 is threaded into the implant 1000 without the assistance of the guidewire 1004. As described above, a non-cannulated removal screw 1010 may be threaded into the central lumen or another lumen to ensure that the non-cannulated removal 1010 screw is substantially centered relative to the implant 1000. A drill bit may be utilized to remove a small amount of implant material prior to threading the non-cannulated removal screw 1010 into the implant 1000 to ensure full thread purchase and to prevent splitting or bulging of the implant 1000 adjacent to the interface with the removal screw 1010.

Figure 13D:
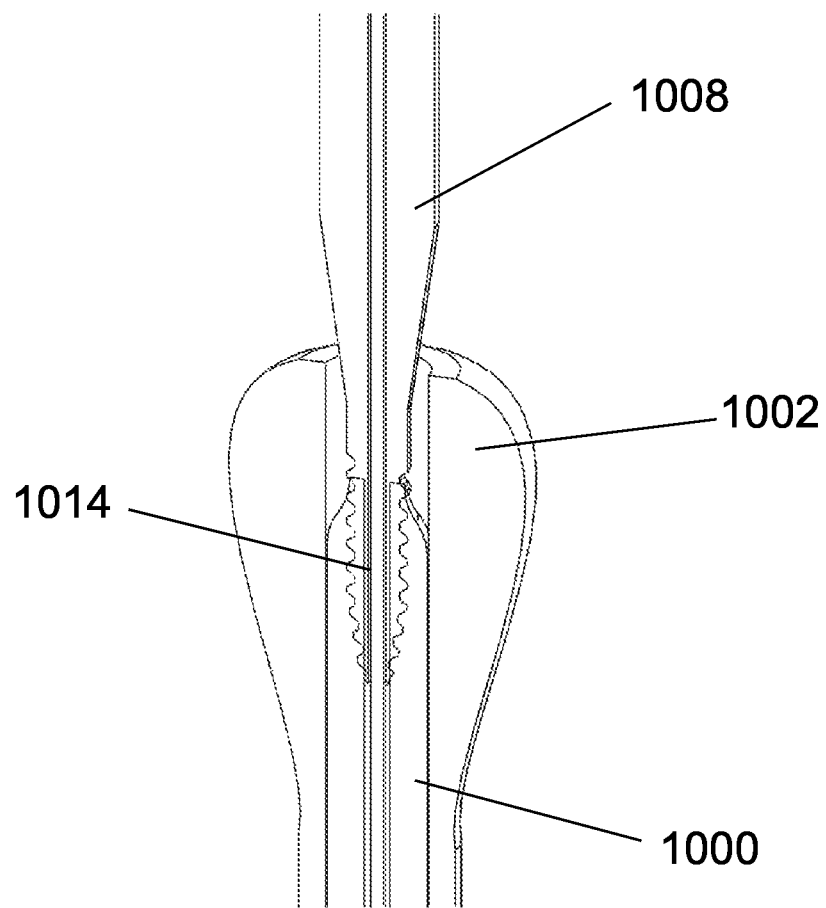
Figure 13E:
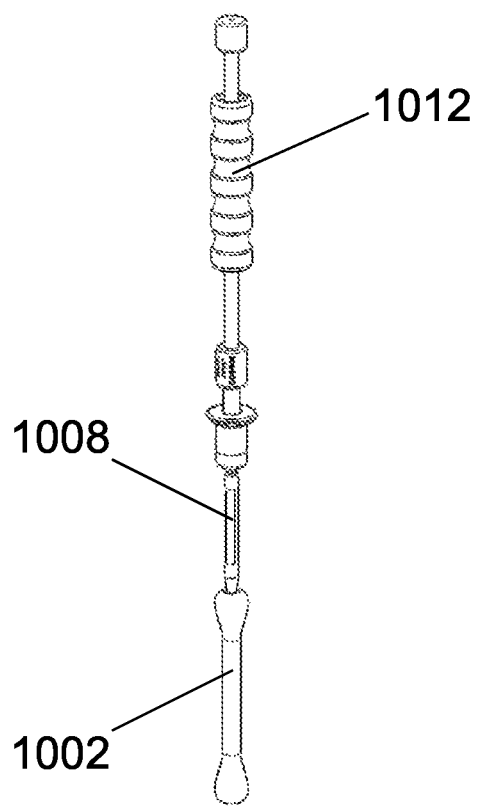
Figure 13F:
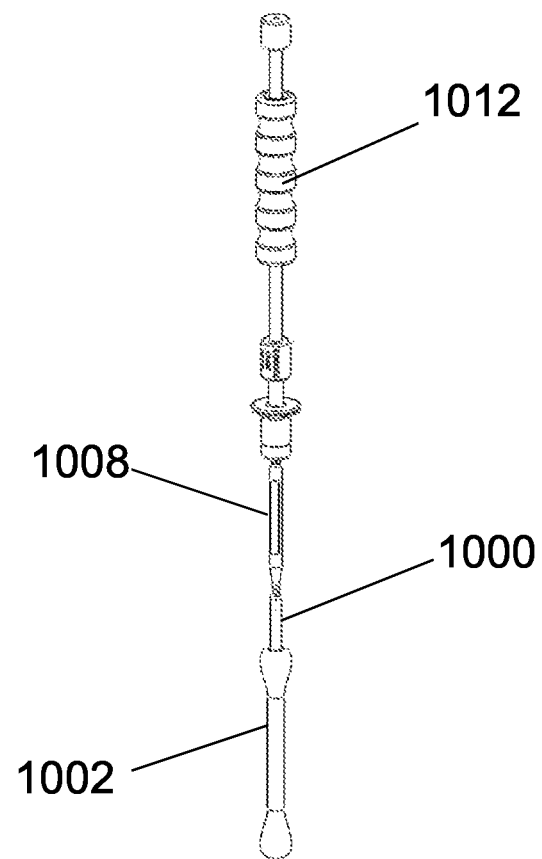
Figure 13G:
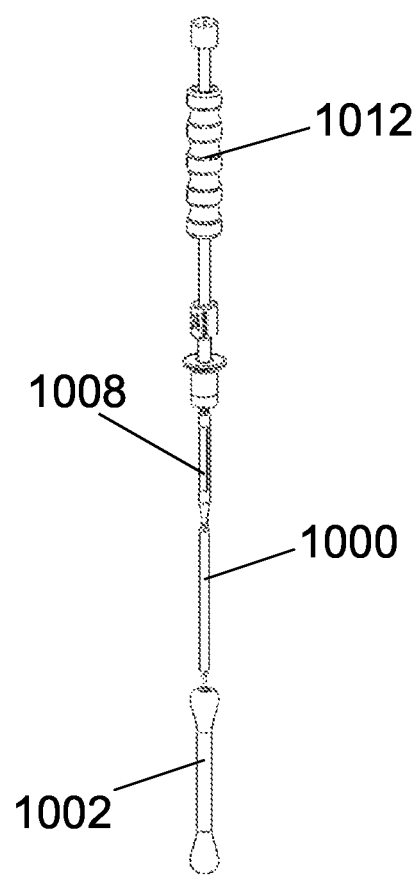

Once the removal screw 1008 is sufficiently threaded into the implant 1000 to achieve a desired purchase, as shown in FIG. 13D, the removal screw 1008 is coupled to a slaphammer 1012, as shown in FIG. 13E. In an embodiment, the removal screw 1008 and the slaphammer 1012 are provided with corresponding quick connect features to facilitate their coupling. In an embodiment, the removal screws snap in, interlock or has other mechanical connection to engage the slaphammer 1012. The implant 1000 may then be removed using the impaction force from the slaphammer 1012, as shown in FIG. 13F and FIG. 13G. In an embodiment, the slaphammer 1012 of the present disclosure allows the removal of the implant 1000 intact by applying the impaction force from the slaphammer 1012 multiple times to remove the implant 1000 incrementally from the intramedullary cavity of the bone 1002.

Figure 14:
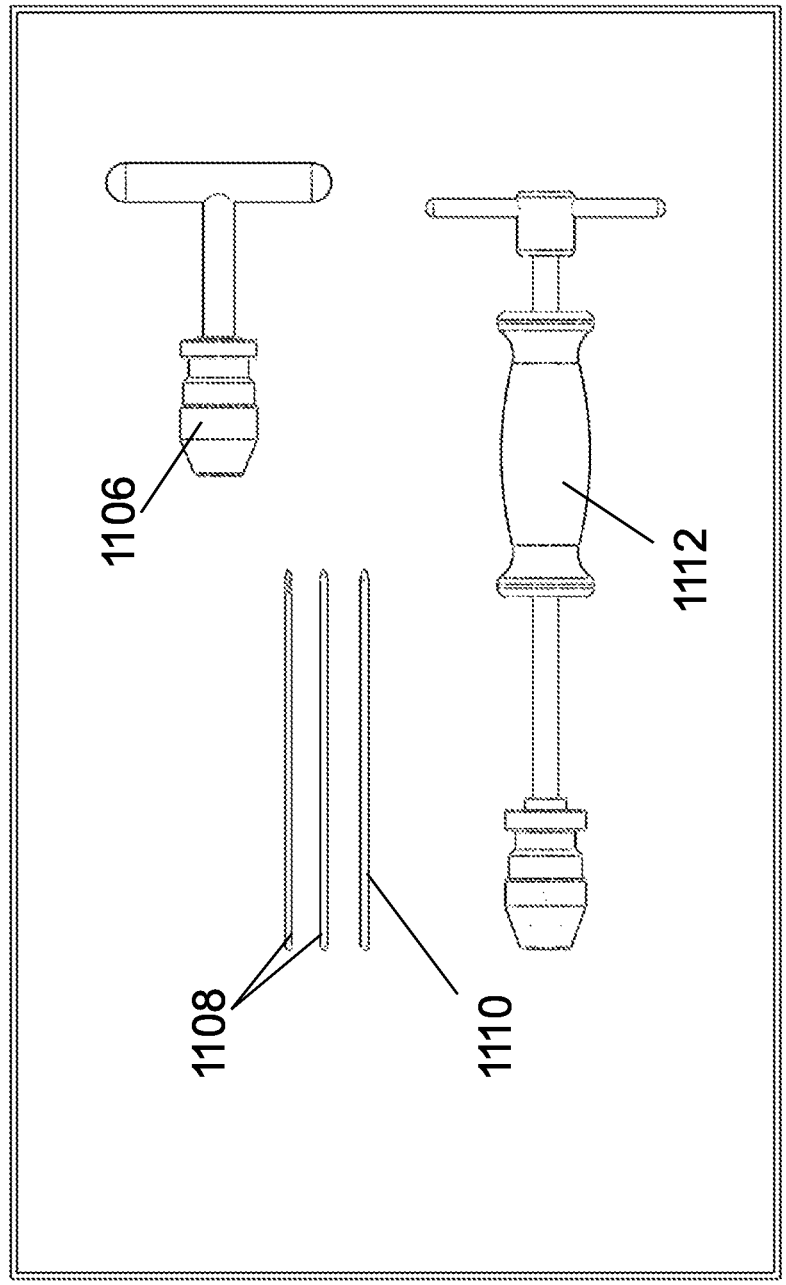
FIG. 14 shows an embodiment of a kit of the present disclosure for removal of an intramedullary device from a bone.

In an embodiment, a system or kit 1120 for removal of an implant formed of a hardened light sensitive liquid from an intramedullary cavity of a bone 1102 is provided. As shown in FIG. 14, the kit 1120 includes one or more threaded guidewires 1108, 1110, a T-handle for threading guidewires 1106, and a slaphammer 1112. The one or more threaded guidewires can include at least one cannulated threaded guidewire 1108 and at least one non-cannulated threaded guidewire 1110. In an embodiment, the threaded guidewires 1108 are flexible for maneuvering the threaded guidewires 1108 to and into the implant 1100. The thread on the guidewires 1108 is designed to engage the implant 1100. In an embodiment, the thread has pitch, root and major diameters and length sized to facilitate an easy insertion of threaded guidewire 1108 into the implant 1100. The thread is also designed to create a pullout interface capable of withstanding forces that exceed the resistance force on the implant 1100 as the implant 110 is removed from the intramedullary cavity, without damaging the implant, i.e. stripping of the implant. In an embodiment, the thread is provided with geometry that allows easy initial engagement between the threaded guidewire 1108 and the implant 1100. In an embodiment, the guidewires 1108 include a blunt, radiused, or conical distal tip followed by a threaded section, where the blunt tip allows the guidewire 1108 to follow a lumen of the implant 1100 and not pierce the lumen. The thread can extend for a desired length of the guidewires 1108. In an embodiment, the T-handle 1106 and the slaphammer 1112 can include a chuck, such as a Jacobs chuck. The chuck allows grabbing the threaded guidewire 1108 by the T-handle 1106 or the slaphammer 1112 anywhere along the length of threaded guidewire 1108. In an embodiment, the T-handle 1106 and the slaphammer 1112 are cannulated.

In an embodiment, shown in FIGS. 15A-15D, the implant 1100 can be removed from the intramedullary cavity of the bone 1102 using the tools of the kit 1120. After access to the implant 1100 inside the intramedullary cavity of the bone 1102 has been gained, a threaded guidewire 1108 may be threaded into the implant 1100. In an embodiment, the threaded guidewire 1108 may be driven into the implant 1100 manually with assistance of a T handle with chuck 1106. In an embodiment, the guidewire 1108 may be driven into the implant 1100 using a power drill. In an embodiment, the threaded guidewire 1108 is threaded into the implant 1100 substantially along the centerline of the implant 1100. In an embodiment, the threaded guidewire 1108 is threaded into the central lumen of the implant 1100.

Figure 15A:
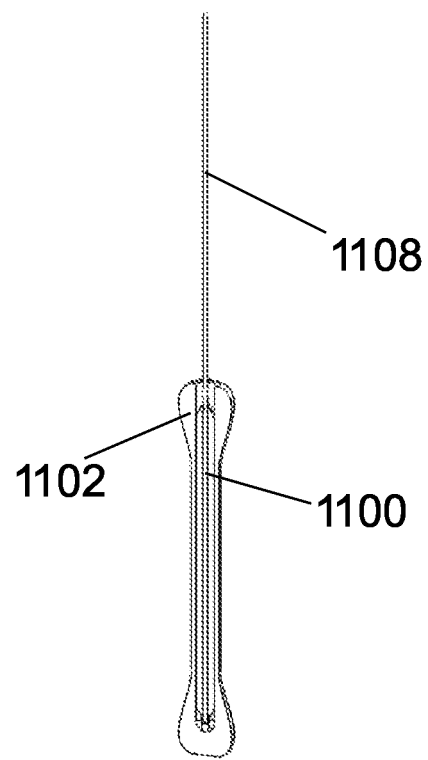
FIGS. 15A-15D show an embodiment of method steps for removing an intramedullary device from a bone using the embodiment kit of FIG. 14.
Figure 15B:
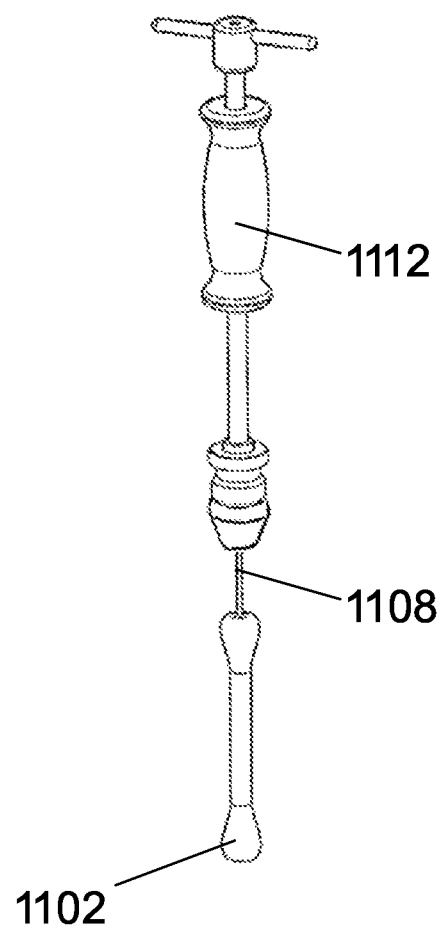
Figure 15C:
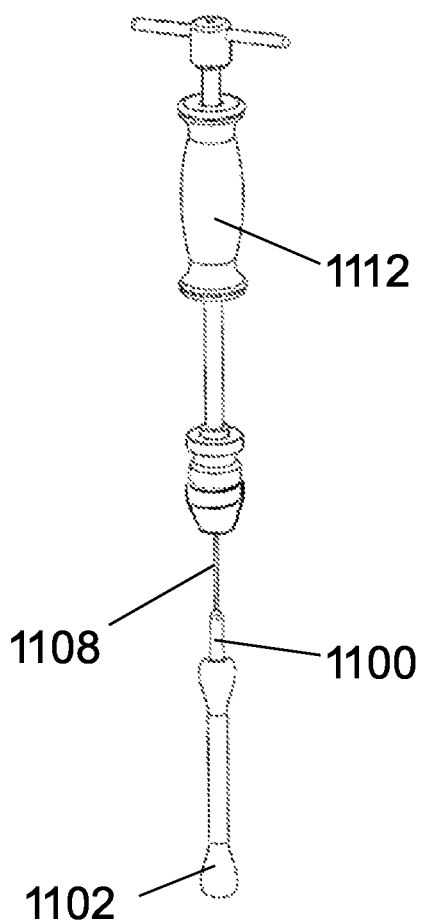
Figure 15D:
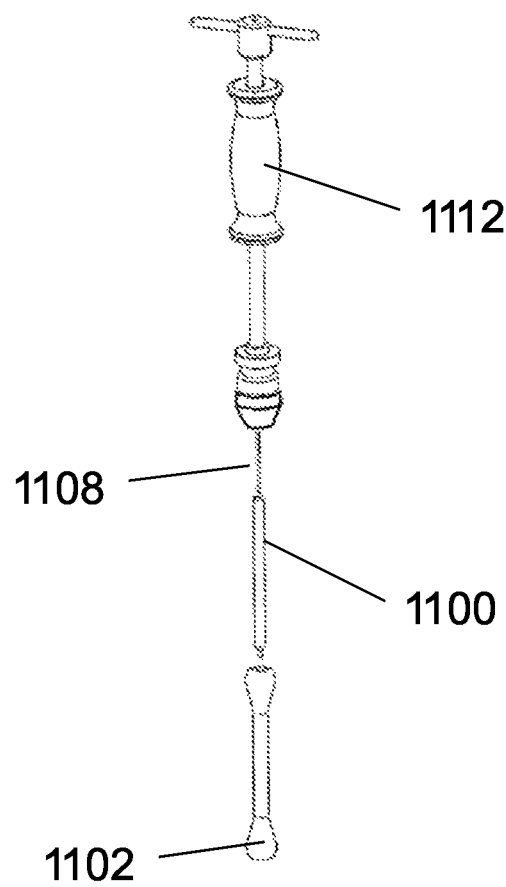

As shown in FIG. 15A, the threaded guidewire 1108 is inserted into the implant 1100 for a desired length to achieve sufficient purchase. Once the threaded guidewire 1108 is sufficiently threaded into the implant 1100, the threaded guidewire 1108 is coupled to a slaphammer 1112, as shown in FIG. 15B. In an embodiment, the threaded guidewire 1108 and the slaphammer 1112 are provided with corresponding quick connect features to facilitate their coupling. In an embodiment, the threaded guidewires snap in, interlock or has other mechanical connection to engage the slaphammer 1112. The implant 1100 may then be removed using the impaction force from the slaphammer 1112. In an embodiment, the slaphammer 1112 of the present disclosure allows the removal of the implant 1100 intact by applying the impaction force from the slaphammer 1112 multiple times to remove the implant 1100 incrementally from the intramedullary cavity of the bone 1102, as shown in FIG. 15C and FIG. 15D.

In an embodiment, a system or kit 1220 for removal of an implant 1200 formed of a hardened light sensitive liquid from an intramedullary cavity of a bone 1202 is provided. As shown in FIG. 16, the kit 1220 includes one or more augers 1206 of varying diameter, and one or more guides 1208. In an embodiment, the kit 1220 also include a drill for driving the augers. In an embodiment, the augers 1206 are designed to facilitate the optimal cutting of the bone pin material. In an embodiment, the augers 1206 are provided with one or more of the following: a self driving, positive rake angle; front and side cutting edges; a relatively flat point angle and a relatively short cutting flute length. Providing an auger 1206 of the present disclosure with one or more of these features can enable the auger 1206 to create large, continuous chips of material and clear these chips of material to the back side of the auger 1206, without binding in flutes of the auger 1206. In an embodiment, at least one auger 1206 is cannulated for advancement over a guidewire 1204. In an embodiment, the augers 1206 are provided with flexible shafts 1214 to allow augers 1206 to enter the intramedullary cavity from off axis access hole and engage the implant 1200.

Figure 17A:
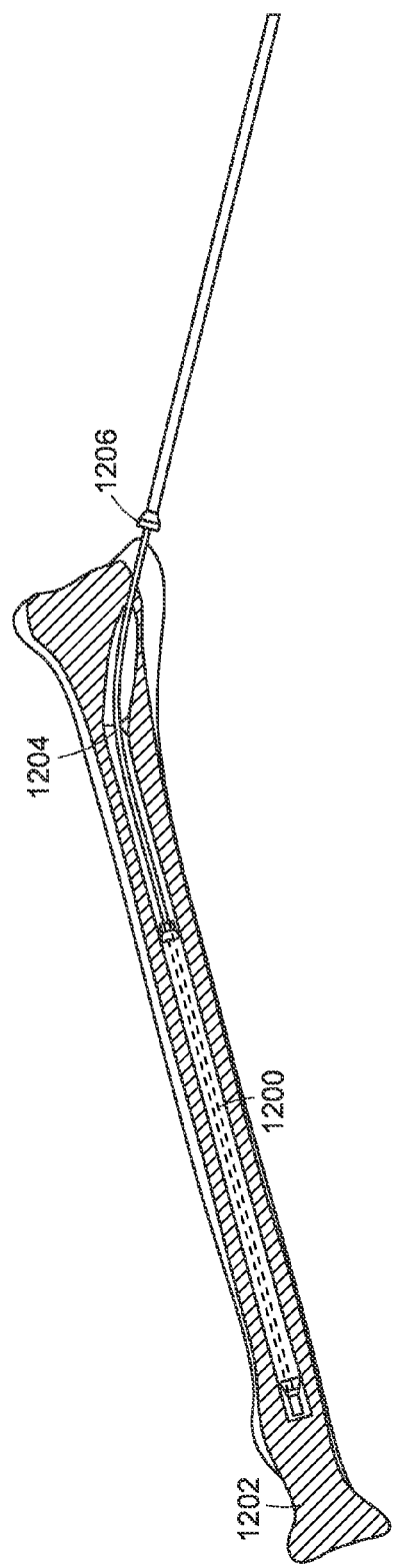
Figure 17B:
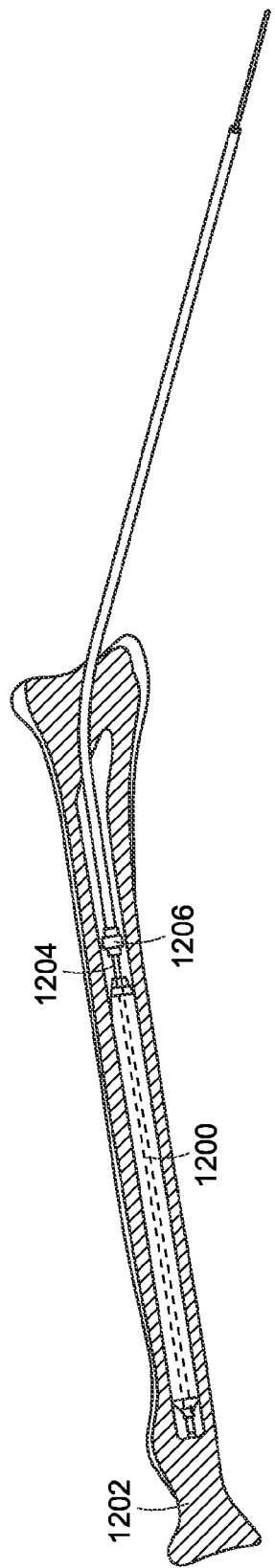

In an embodiment, a method for the removal of the implant 1200 from the bone 1202 using the tools of the kit 1220 is provided, as shown in FIGS. 17A-17F. In reference to FIG. 17A and FIG. 17B, after access to the implant 1200 inside the intramedullary cavity of the bone 1202 has been gained, flexible augers 1206 can be used to ream out the implant 1200. In an embodiment, a power drill can be used to drive the flexible augers 1206. In an embodiment, the flexible augers 1206 are used in a sequential manner to progressively ream out the implant 1200. As shown in FIG. 17C and FIG. 17D, a first auger 1206A having a first diameter is driven through the implant 1200. The first auger 1206A is followed by a second auger 1206B having a second diameter, which is larger than the first diameter, as shown in FIG. 17E and FIG. 17F, further followed by a third auger having a third diameter having a larger diameter than the second diameter, and so on. In an embodiment, additional augers 1206 are used until the implant 1200 is substantially removed. The implant fragments generated during the removal procedure can be removed by suction or irrigation, as is described below.

In an embodiment, the flexible augers 1206 may be inserted along a guidewire 1204. In an embodiment, the guidewire 1204 may be inserted into a central lumen of the implant 1200, such that the guidewire 1204 passes substantially through the centerline of the implant 1200. In an embodiment, if the implant 1200 is not symmetrical about the central lumen, another lumen may be created such that the guidewire 1204, when inserted into the newly-drilled lumen, passes substantially through the centerline of the implant 1200. Once the guidewire 1204 is placed into the implant 1200, flexible augers 1206 may be advanced over the guidewire 1204 to enable self centering of the augers 1206 relative to the implant 1200. In an embodiment, the flexible augers 1206 may be used without a guidewire 1204, either along the central lumen or another lumen created in the implant 1200.

Figure 18A:
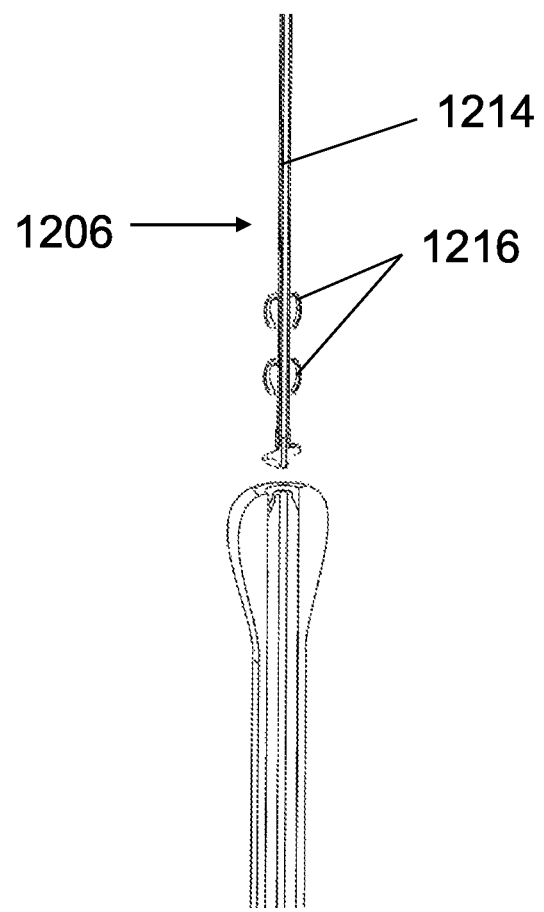
FIGS. 18A-18D show an embodiment of method steps for removing an intramedullary device from a bone using the embodiment kit of FIG. 16.
Figure 18B:
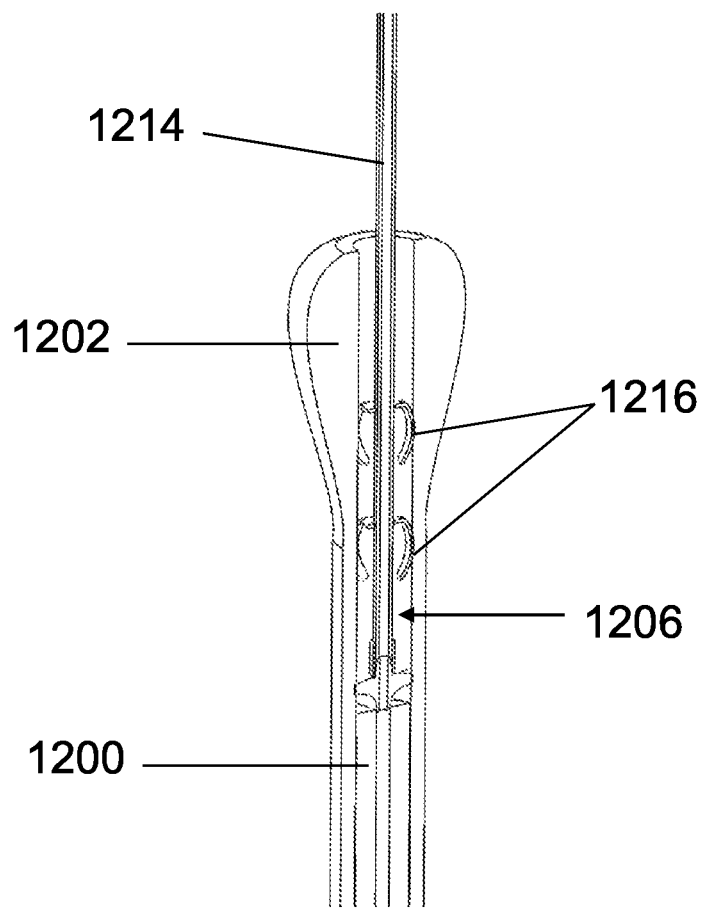
Figure 18C:
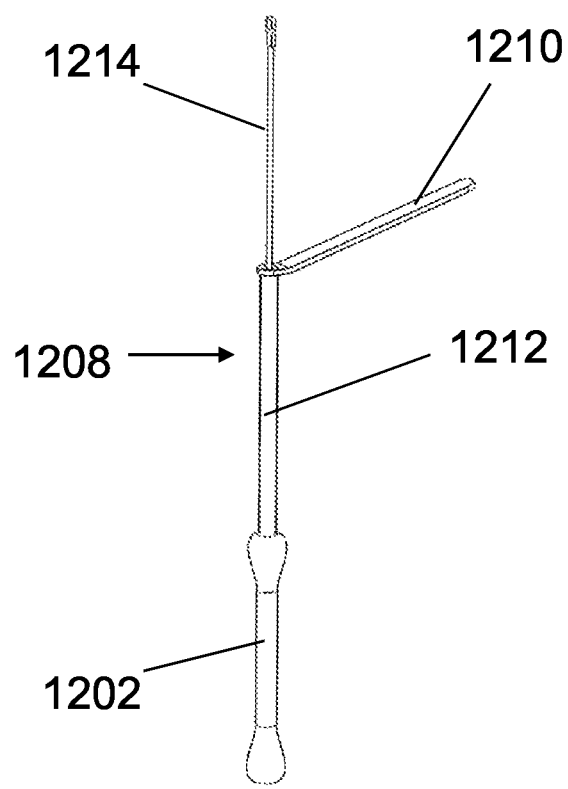
Figure 18D:
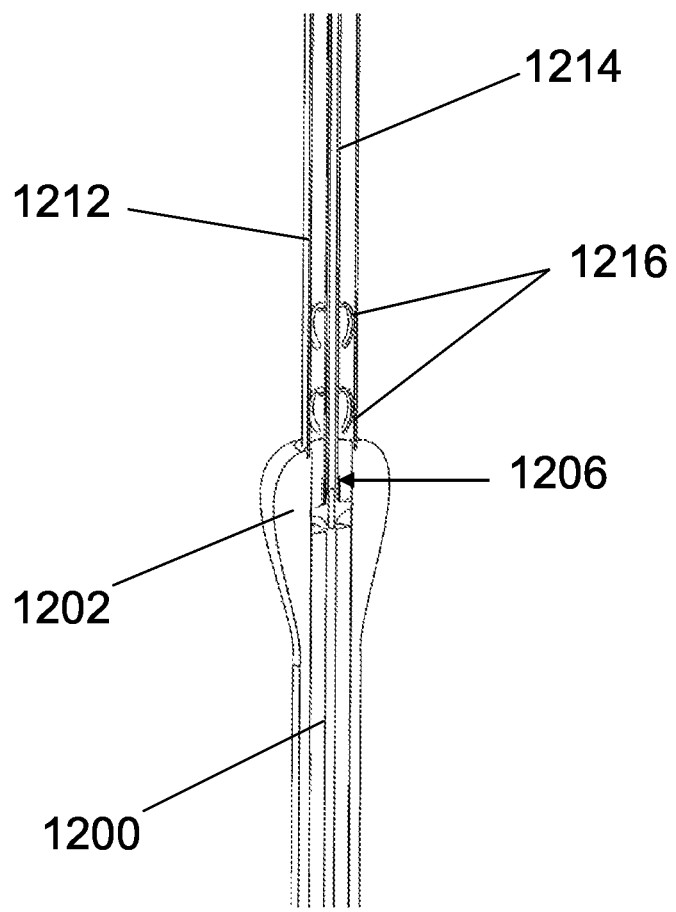

In an embodiment, the augers 1206 can be provided with means for self centering as the auger 1206 travels through the implant 1200. In reference to FIG. 18A, the auger 1206 includes a plurality of springs 1216 disposed along a section of the auger shaft 1214. When the auger 1206 is inserted into the lumen of the implant 1200, the springs 1216 act to center the auger 1206 and maintain the auger 1206 centered as the auger 1206 advances though the implant 1200, as shown in FIG. 18B. In an embodiment, the kit 1220 also includes a guide 1208 for centering the augers 1206 as the auger 1206 travels through the implant 1200. As shown in FIG. 18C, the guide 1208 includes a handle 1210 and a tube 1212 designed to receive an auger 1206. The tube 1212 is designed to engage the implant 1200 and to provide support for the auger 1206 as the auger 1206 advances through the implant 1200. In an embodiment, the tube 1206 also aids in centering the auger 1206 inside the implant 1200. In an embodiment, the guide 1208 trails a slight distance behind the leading tip of the auger 1206 to provide continual support and centering to the auger 1206 throughout the process. The guide may be flexible. It should be understood that the self-centering means and the guide 1208 can be used simultaneously, as shown in FIG. 18D. In an embodiment, the tube 1212 of the guide 1208 is comprised of a tube that is free to rotate relative to the handle 1210 of the guide 1208. In an embodiment, this may enable the tube 1212 to be driven, by hand or a power drill, into the implant 1200 in advance of the leading tip of the auger 1206. The auger 1206 would then be used to remove the material within the tube 1212. The tube 1212 would then be advanced again and the operation repeated.

There are many methods and systems for removing debris during an orthopedic surgery that are known in the art and within the spirit and scope on the presently disclosed embodiments. Suitable methods for removing remaining debris include, but are not limited to, suction, vacuum removal, irrigation, and combinations thereof. In general, a suction system may include a source of suction and a conduit to provide limited access to the surgical site coupled to the suction source in order to provide suction at the distal end of the conduit. Other suitable methods and systems are described in U.S. Pat. No. 5,520,668 entitled "Medical Suction System and Method," U.S. Pat. No. 6,908,455 entitled "Surgical Suction Probe System with an Easily Cleaned Internal Filter," and U.S. Pat. No. 7,481,791 entitled "Surgical Suction Irrigator."

In an embodiment, an implant removal system includes a wire, having at its distal end, a toggle configured to move about a hinge from a first position to a second position and back again; and a plurality of burrs configured to be positioned over a longitudinal axis of the wire, wherein the plurality of burrs have incrementally increasing diameters for removing portions of the implant.

In an embodiment, an implant removal system includes a wire for guiding the system through an implant; a toggle, situated at a distal end of the wire, wherein the toggle is configured to move about a hinge from a first position to a second position and back again, and wherein the toggle is configured to secure the system in place within the implant; and a plurality of burrs configured to be positioned over a longitudinal axis of the wire, wherein the plurality of burrs include cutting portions for removing portions of the implant.

In an embodiment, a method of using an implant removal system includes positioning a wire through an implant, the wire having at its distal end, a toggle configured to move about a hinge from a first position to a second position and back again; and inserting a plurality of burrs over a longitudinal axis of the wire, wherein the plurality of burrs have incrementally increasing diameters for removing portions of the implant.

In an embodiment, a method for removing an intramedullary implant from a bone includes navigating a guidewire into an intramedullary cavity of the bone; inserting the guidewire into a lumen of an intramedullary implant located in the intramedullary cavity of the bone; advancing a removal screw over the guidewire to the intramedullary implant; threading the removal screw into the lumen of the intramedullary implant to engage the removal screw to the intramedullary implant; and applying impaction force on the removal screw to remove the intramedullary implant from the intramedullary cavity.

In an embodiment, a method for removing an intramedullary implant from a bone includes advancing a guidewire into an intramedullary cavity of a bone; inserting the guidewire into a lumen of an intramedullary implant located in the intramedullary cavity of the bone; advancing a first auger having a first diameter over the guidewire toward the intramedullary implant; and engaging the first auger to a distal end of the intramedullary implant to remove at least a portion of the intramedullary implant.

In an embodiment, a method for removing an intramedullary implant from a bone includes threading a removal screw into a lumen of the intramedullary implant to engage the removal screw to the intramedullary implant and applying impaction force on the removal screw to remove the intramedullary implant from the intramedullary cavity.

In an embodiment, a method for removing an intramedullary implant from a bone includes inserting a threaded guidewire into a lumen of the intramedullary implant to engage the threaded guidewire to the intramedullary implant and applying impaction force on the threaded guidewire to remove the intramedullary implant from the intramedullary cavity.

In an embodiment, a system for removal of an implant from a bone includes one or more guidewires sufficiently designed to be inserted into a lumen of an intramedullary implant in a bone; one or more removal screws, wherein the removal screws are cannulated such that the removal screws can be advanced over the guidewire to the intramedullary implant; the removal screws include a threaded distal portion for engagement of the implant; and a slaphammer designed to engage the removal screws and to apply impaction force on the removal screw engaged to the intramedullary implant to remove the intramedullary implant from the bone.

In an embodiment, a system for removal of an implant from a bone includes one or more removal screws having a threaded distal portion for engagement of the implant and a slaphammer designed to engage the removal screws and to apply impaction force on the removal screw engaged to the intramedullary implant to remove the intramedullary implant from the bone.

In an embodiment, a system for removal of an implant from a bone includes one or more threaded guidewires having a threaded distal portion for engagement of the implant and a slaphammer designed to engage the threaded guidewires and to apply impaction force on the threaded guidewires engaged to the intramedullary implant to remove the intramedullary implant from the bone.

In an embodiment, a system for removal of an implant from a bone includes a plurality of augers of varying size, a drill for driving the augers, and optionally, guides designed to provide support and center the augers as the augers are advanced through the implant. In an embodiment, at least one auger is cannulated and the system includes a guidewire over which the auger can be advanced through the implant.

In an embodiment, a kit for removal of an implant from a bone includes one or more guidewires sufficiently designed to be inserted into a lumen of an intramedullary implant in a bone; one or more removal screws, wherein the removal screws are cannulated such that the removal screws can be advanced over the guidewire to the intramedullary implant; the removal screws include a threaded distal portion for engagement of the implant; and a slaphammer designed to engage the removal screws and to apply impaction force on the removal screw engaged to the intramedullary implant to remove the intramedullary implant from the bone.

In an embodiment, a kit for removal of an implant from a bone includes one or more removal screws having a threaded distal portion for engagement of the implant and a slaphammer designed to engage the removal screws and to apply impaction force on the removal screw engaged to the intramedullary implant to remove the intramedullary implant from the bone.

In an embodiment, a kit for removal of an implant from a bone includes one or more threaded guidewires having a threaded distal portion for engagement of the implant and a slaphammer designed to engage the threaded guidewires and to apply impaction force on the threaded guidewires engaged to the intramedullary implant to remove the intramedullary implant from the bone.

In an embodiment, a kit for removal of an implant from a bone includes a plurality of augers of varying size, a drill for driving the augers, and optionally, guides designed to provide support and center the augers as the augers are advanced through the implant. In an embodiment, at least one auger is cannulated and the kit includes a guidewire over which the auger can be advanced through the implant.

All patents, patent applications, and published references cited herein are hereby incorporated by reference in their entirety. It will be appreciated that several of the above-disclosed and other features and functions, or alternatives thereof, may be desirably combined into many other different systems or applications.

What is claimed is:

1. A method for removing an existing hardened intramedullary implant from a bone comprising:

identifying a location of the existing hardened intramedullary implant located in an intramedullary cavity of the bone, wherein the existing hardened intramedullary implant comprises a light sensitive liquid in a hardened state contained within a polymeric balloon, the light sensitive liquid changes in state from a flowable state to the hardened state upon exposure to light from a light source, and wherein the polymeric balloon contacts the bone in the intramedullary cavity to form a frictional engagement between the polymeric balloon and the bone;

subsequent to the identifying the location of the existing hardened intramedullary implant, threading a flexible guidewire having threads at a distal end into the existing hardened intramedullary implant located in the intramedullary cavity of the bone;

wherein threading the flexible guidewire into the existing hardened intramedullary implant comprises engaging the threads of the flexible guidewire into the existing hardened intramedullary implant; and applying impaction force on the flexible guidewire to remove the existing hardened intramedullary implant from the intramedullary cavity, wherein the engagement between the threads of the flexible guidewire and the existing hardened intramedullary implant create a pullout interface between the threads of the flexible guidewire and the existing hardened intramedullary implant to withstand forces that exceed a resistance force on the existing hardened intramedullary implant due to friction between the balloon and the bone in the intramedullary cavity, to pullout the existing hardened intramedullary implant from the intramedullary cavity of the bone without stripping of the existing hardened intramedullary implant.

2. The method of claim 1, wherein threading the flexible guidewire into the existing hardened intramedullary implant comprises inserting the flexible guidewire into a pre-existing lumen in the intramedullary implant such that the guidewire passes substantially along a centerline of the intramedullary implant.

3. The method of claim 1, wherein threading the flexible guidewire into the existing hardened intramedullary implant comprises inserting the flexible guidewire into a drilled lumen in the intramedullary implant such that the guidewire passes substantially along a centerline of the intramedullary implant.

4. The method of claim 1, wherein the impaction force is applied multiple times to remove the existing hardened intramedullary implant from the bone.

5. The method of claim 1, wherein the impaction force is applied on the flexible guidewire by a slaphammer.

6. The method of claim 1, wherein the flexible guidewire is inserted into the existing hardened intramedullary implant substantially along a centerline extending in a longitudinal direction of the existing hardened intramedullary implant.

7. A method for removing an existing hardened intramedullary implant from a bone comprising:

identifying a location of the existing hardened intramedullary implant located in an intramedullary cavity of the bone, wherein the existing hardened intramedullary implant is formed by introducing a light-sensitive liquid in a flowable state into a polymeric balloon to expand the polymeric balloon from a deflated state to an inflated state inside the intramedullary cavity and exposing the light-sensitive liquid to light from a light source to change the light sensitive liquid to a hardened state within the polymeric balloon, and wherein the polymeric balloon contacts the bone in the intramedullary cavity to form a frictional engagement between the polymeric balloon and the bone;

subsequent to the identifying the location of the existing hardened intramedullary implant, threading a threaded tip of a flexible guidewire into the existing hardened intramedullary implant located in the intramedullary cavity of the bone, wherein threading the flexible guidewire into the existing hardened intramedullary implant comprises engaging the threads of the threaded tip of the flexible guidewire into the existing hardened intramedullary implant; and impacting the flexible guidewire with a slaphammer to remove the existing hardened intramedullary implant from the intramedullary cavity of the bone, wherein the engagement between the threads of the flexible guidewire and the existing hardened intramedullary implant create a pullout interface between the threads of the flexible guidewire and the existing hardened intramedullary implant to withstand forces that exceed a resistance force on the existing hardened intramedullary implant due to friction between the balloon and the bone in the intramedullary cavity, to pullout the existing hardened intramedullary implant from the intramedullary cavity of the bone without stripping of the existing hardened intramedullary implant.

8. The method of claim 6, wherein the existing hardened intramedullary implant is removed from the bone incrementally by impacting the guidewire multiple times.

9. The method of claim 7, wherein the flexible guidewire is inserted into the existing hardened intramedullary implant substantially along a centerline extending in a longitudinal direction of the existing hardened intramedullary implant.

* * * * *